United States Patent [19]

Fritz et al.

[11] 4,401,454

[45] Aug. 30, 1983

[54] GROWTH REGULATION METHODS

[75] Inventors: Charles D. Fritz, North Wales, Pa.; Wilbur E. Evans, Kuala Lumpur, Malaysia; Anson R. Cooke, Hatfield, Pa.

[73] Assignee: Union Carbide Corporation, Danbury, Conn.

[21] Appl. No.: 186,461

[22] Filed: Oct. 4, 1971

Related U.S. Application Data

[63] Continuation-in-part of Ser. No. 869,386, Oct. 24, 1969, Pat. No. 4,374,661, which is a continuation-in-part of Ser. No. 693,698, Dec. 27, 1967, abandoned, which is a continuation-in-part of Ser. No. 617,860, Feb. 23, 1967, abandoned.

[51] Int. Cl.$^3$ .................................... A01N 57/00
[52] U.S. Cl. ........................................ 71/76; 71/78; 71/86
[58] Field of Search ................... 71/86, 76, 78; 260/502.4; 424/198

[56] References Cited

U.S. PATENT DOCUMENTS

| | | | |
|---|---|---|---|
| 3,531,549 | 9/1970 | Randall | 71/86 |
| 3,551,528 | 12/1970 | Randall | 71/86 |
| 3,600,435 | 8/1971 | Randall et al. | 71/86 |
| 3,626,037 | 12/1971 | Randall et al. | 71/86 |
| 3,679,780 | 7/1972 | Randall et al. | 71/86 |
| 3,713,805 | 1/1973 | Randall et al. | 71/86 |
| 3,728,381 | 4/1973 | Randall et al. | 71/86 |
| 3,733,192 | 5/1973 | Harris et al. | 71/77 |
| 3,771,992 | 11/1973 | Hofer et al. | 71/87 |
| 3,808,265 | 4/1974 | Randall et al. | 71/86 |
| 3,821,864 | 7/1974 | Stottlemyer | 71/86 |
| 3,825,635 | 7/1974 | Hofer et al. | 71/86 |

*Primary Examiner*—Glennon H. Hollrah
*Attorney, Agent, or Firm*—Robert C. Brown; Dale L. Carlson; John A. Shedden

[57] ABSTRACT

A growth regulation process involving certain phosphonic acid compounds having the general formula:

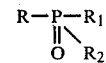

The growth regulation process of the present invention relates mainly, though not entirely, to the inducement of an ethylene response or ethylene-type response in plants and part thereof including, but not limited to, stems, roots, leaves, flowers, buds, and harvested as well as unharvested fruit.

The method of the present invention produces a wide variety of plant growth responses including:
1. Increasing yields
2. Auxin activity
3. Inhibition of terminal growth, control of apical dominance, increase in branching and increase in tillering
4. Changing bio-chemical composition of plant or portions thereof
5. Abscission of foliage, flowers and fruit
6. Hastening ripening and color promotion in fruit
7. Increasing flowering and fruiting
8. Abortion or inhibition of flowering and seed development
9. Prevention of lodging
10. Stimulation of seed germination and breaking of dormancy
11. Resistance to freeze injury
12. Hormone or epinasty effects
13. Interaction with other growth regulators
14. Interaction with herbicides
15. Disease resistance.

31 Claims, No Drawings

GROWTH REGULATION METHODS

This application is a Continuation-In-Part application based on prior co-pending application Ser. No. 869,386, filed Oct. 24, 1969 now U.S. Pat. No. 4,374,661 and entitled "Growth Regulation Process", which in turn was a Continuation-In-Part application based on prior co-pending application Ser. No. 693,698, filed Dec. 27, 1967 and entitled "Phosphonic Compound Growth Regulation Process", now abandoned, which inturn was a Continuation-In-Part application based on prior co-pending application Ser. No. 617,860, filed Feb. 23, 1967 and entitled "Growth Regulation Process Utilizing Phosphonic Compounds", now abandoned.

The present invention relates to the use of certain phosphonic acid compounds in order to induce growth regulating responses exemplified, but not necessarily limited to, ethylene responses or ethylene-type responses.

The induction of an ethylene response in plant growth by other means has been known for some time in the art. See "Plant Biochemistry" by James Bonner and J. E. Varner (1965), pages 641 to 664.

A fairly well known ethylene response is the use of gaseous ethylene in the ripening of bananas which has been carried out on a commercial scale for many years. It is also known to employ ethylene in essentially gaseous form to stimulate flower initiation in pineapples. See "Hormonal Control of Plant Growth" by N. S. Parihar (1964), pages 69 to 79. Here, ethylene was applied on a commercial scale using cumbersome equipment to drench the pineapple plants with ethylene - saturated liquid. Similar, but less powerful effects on plant tissues have been caused by other unsaturated hydrocarbic gases.

The mechanism by which ethylene and the other gases affect the growth cycle of plants is far from fully understood, but it is clear that they do play a role. It will be seen that the phoshonic acid compounds and derivatives used to practice the present invention contain in their structures molecular configurations which are capable of breaking down into ethylene or like compounds although there is no intention to limit the present invention to this theory or any other theory.

The use of certain other phosphonate compounds in the agricultural art is known for herbicidal purposes as set forth in U.S. Pat. No. 2,927,014 and No. 3,223,514. However, it will be seen that the compounds disclosed in the aforesaid two patents do not produce the growth regulating responses for ethylene-type response of the present invention.

Instead, the present invention involves the inducement of a plant regulating response or an ethylene-type response through the application of compounds at the plant site having the following generic formula:

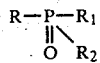

where
R is selected from this group consisting of halo-ethyl and phosphono-ethyl; and
R₁ and R₂ are selected from the group consisting of
1. Chlorine atom and a hydroxy group;
2. The group —OR₃ and the group —O—CH₂R₃ where each R₃ is one member of the group of unsubstituted aryl, substituted aryl and heterocyclic groups;
3. The group —OR₃ and the group —O—CH₂R₃ where each R₃ is a different member of the group of hydrogen, unsubstituted alkyl, substituted alkyl, unsubstituted aryl, substituted aryl, heterocycle, alkene and alkyne, provided that when one R₃ is selected from the group of unsubstituted alkyl, substituted alkyl, alkene and alkyne, the other R₃ is selected from the group of unsubstituted aryl, substituted aryl and heterocycle.
4. Together R₁ and R₂ represent the group

(R₄ and R₅ are each connected to the phosphorous atom by a separate single bond) where one of R₄ and R₅ is —O— and the other is selected from the group of —O—; —OCH₂; —CO—O— and CONH and R₆ represents a cyclic group selected from the group consisting of benzene, substituted benzene, heterocyclic ring and substituted heterocyclic ring;
5. One of R₁ and R₂ is —OR₇ and the other is

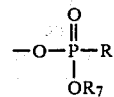

wherein each R₇ is the same or different and is selected from the group of hydrogen, unsubstituted alkyl, substituted alkyl, unsubstituted aryl, substituted aryl and a heterocycle group, and wherein R is as defined hereinbefore.

Reference is hereby made to the following prior co-pending applications, the disclosures of which are hereby incorporated by reference:
(1) Application Ser. No. 617,860
  Filed: Feb. 23, 1967
  Inventors: Charles D. Fritz and Wilbur F. Evans
  Title: Growth Regulation Process Utilizing Phosphonic Compounds
(2) Applications Ser. No. 617,820 and No. 617,819
  Both Filed: Feb. 23, 1967
  Inventor: David Randall
  Title of Both: Phosphonic Acid Esters and Method for Their Preparation
  Assignee: General Aniline and Film Corporation The foregoing applications specified hereinabove basically disclose preparation techniques for the compounds utilized in the method of the present invention.

Where the term "halo" is used, it is to be understood that this term means the familiar halogens, i.e. fluorine, chlorine, bromine and iodine, so long as an operative growth regulation compound is obtained.

With reference to the general formula utilized in the method of the present invention, preferred groups for substituent R are haloethyl, for example, 2-chloroethyl, 2-bromoethyl and 2-iodoethyl. Preferred half-esters of the phosphonic acid moiety include the 2-chloroethyl mono-ester and the o-hydroxyphenyl mono-ester. Preferred diesters include the diphenyl and the bis (2-oxo-1-pyrrolidinyl-methyl) esters and as mixed esters, the 2-hydroxyphenyl ester with an alkyl or alkenyl or aryl radical for example, ethyl, isopropyl, propynyl, butyl, octyl, hexadecyl or phenyl radicals. Aryl groups are preferably monocyclic, and bi- or polycyclic aryl groups may be used provided a group to render them soluble (e.g. a sulphonate group), is present thereon.

The term "alkyl" as used herein is intended to include the analogous compounds which have the same growth promotion properties and includes for example cycloalkyl groups, sucy as cyclohexyl. Preferred alkyl groups are those having up to preferably 18 carbon atoms because above this range, the derivatives are less soluble.

Preferred cyclic esters include those formed with pyrocatechol or mono- or polyhalopyrocatechol derivatives, for example 4-chloropyrocatechol or tetrachloropyrocatechol; with salicyclic acid, with saligen; and with 2,3-pyridinediol. Another preferred derivative is the acid chloride.

It will be seen that the preferred phosphonic derivative to be used in connection with the present invention is 2-chloroethyl-phoshonic acid or its immediate derivatives as will be discussed in more detail hereinafter.

The phosphonic acid compound used in the process of the present invention have been found to display a wide variety of plant growth regulating properties or ethylene-type responses, depending upon the concentration used, the formulation employed and the type of plant species treated. While the compounds used in the present invention may be regarded as achieving an ethylene response or an ethylene-type response, the present invention is not necessarily limited thereto since it is recognized that certain growth regulating responses achieved through the practice of the present invention may not be regarded as being technically traditional or known or to be discovered ethylene responses or even ethylene-type responses. Hence, it is preferred to regard the results achieved in the practice of the present invention as growth regulating responses.

In view of the foregoing, it can be seen that the term "method for regulating plant growth" or the term "growth regulation process" or the use of the words "growth regulation" or other terms using the word "regulate" as used in the specification and in the claims mean a variety of plant responses which attempt to improve some characteristic of the plant as distinguished from herbicidal action, the intention of which is to destroy or stunt a growth of a plant. For this reason the compounds used in the practice of this invention are used in amounts which are non-phytotoxic with respect to the plant being treated.

Nevertheless, the phosphonic acid derivatives connected with the present invention can sometimes be used in a herbicidal context, for instance, to stimulate the growth of dormant rhizomes in order to make such rhizomes more susceptible to a herbicide. However, even here the phosphonic acid derivatives used in the present invention are not themselves in any practical sense herbicides since they promote the growth of the unwanted plant or otherwise make it vary susceptible to a true herbicide. Thus, the present invention can be carried out in conjunction with or in the presence of other compounds or mixtures which are herbicides.

By virtue of the practice of the present invention a wide variety of plant growth responses, generally ethylene responses or ethylene-type responses have been achieved, including the following
1. Increasing yields
2. Auxin activity
3. Inhibition of terminal growth, control of apical dominance, increase in branching and increase in tillering
4. Changing bio-chemical compositions of plant
5. Abscission of foliage, flowers and fruit
6. Hastening ripening and color promotion in fruit
7. Increasing flowering and fruiting
8. Abortion or inhibition of flowering and seed development
9. Prevention of lodging
10. Stimulation of seed germination and breaking of dormancy
11. Resistance to freeze injury
12. Hormone or epinasty effects
13. Interactions with other growth regulators
14. Interactions with herbicides
15. Disease resistance It is intended that as used in the appended claims the term "method for regulating plant growth" or "method for inducing an ethylene response" or "method of inducing an ethylene-type response" means the achievement of any of the aforementioned fifteen categories of response as well as any other modification of plant, seed, fruit, vegetable (whether the fruit or vegetable is unharvested or have been harvested) so long as the net result is to increase growth or benefit any property of the plant, seed, fruit or vegetable as distinguished from herbicidal action (unless the present invention is practiced in conjunction with or in the presence of a herbicide). The term "fruit" as used herein and in the appended claims is to be understood as meaning anything of economic value that is produced by the plant.

Certain preliminary details connected with the foregoing fifteen categories should make for a better appreciation of the invention.

1. Increasing Yields:

The phosphonic acid derivatives are capable of increasing yields of many plants, including, but not limited to small grains, particularly oats (*Avena sativa*), wheat (*Triticum aestivum*), and barley (*Hordem spp.*); and of increasing yields of other types of plants, such as beans and of cotton (*Gossypium hirsutum*);

2. Auxin Activity:

When applied for instance as a lanolin paste, to one side of a decapitated sunflower hypocotyl the phosphonic acid derivatives are capable of inducing bending of the hypocotyl away from the side of the application; they are also capable of inducing sprouting of underground rhizomes of monocotyledonous and dicotyledonous plants; of causing cell proliferation; and of inducing rooting, as evidenced by the production of large numbers of root primordia over the entire stem length of tomato plants (*Lycopersicon esculentum*) after these have been sprayed with an aqueous solution thereof - this type of response makes it possible to root cuttings either when taken from treated plants or after treatment of their cut ends.

3. Inhibition of Terminal Growth, Control of Apical Dominance, Increase in Branching, and Increase in Tillering:

These types of plants growth response can be produced on a variety of plant species when they are treated with the phosphonic acid derivatives including privet (*Ligustrum ovalifolium*), blueberry (*Vaccinum corymbosum*), azalea (*Rhododendron obtusum*), soybeans (*Glycine mas.*), snapbeans (*Phaseolus vulgaris*), tomatoes (*Lycopersion esculentum*), alligator weed (*Alternanthua philoxeroides*) and monoctyledons such as rice (*Oryza* sativa), johnsongrass (*Sorghum halopense*) and wild oats (*Avena fatua*). This type of response can also be of value in the control of roadside grasses. It has been suggested that the removal of the lead bud (e.g. by pinching) should allow growth of auxiliary buds; but is is generally found that on removal of the lead bud one of the auxiliary buds takes over the activity and dominance of the lead bud. The use of the phosphonic acid derivatives, however, usually retards the activity of the lead bud for a while but then later restores the lead bud to normal growth, with production of normal flowers and normal fruit; and thus one avoids the permanent loss of buds inevitably associated with pinching. However, some plant species respond differently when treated with the phosphonic acid derivatives for control of apical dominance - growth inhibition may extend to include not only the lead bud but also lateral buds along the stem. Examples of such plants are tobacco (*Nicotiana tabacum*) and chrysanthemum (Chrysanthemum sp.) - this type of response is useful for preventing sucker growth from lateral buds on tobacco.

4. Changing Biochemical Composition of Plant:

The phosphonic acid derivatives are capable of measurably increasing the leaf area relative to the stem area in many plants, and the increased ratio of leaves to stem results in an increase in total protein on a per plant basis, and modification of the protein, carbohydrate, fat, nicotine and sugar within the treated plant.

5. Abscission of Foliage, Flowers and Fruit:

The phosphonic acid derivatives have been found to accelerate abscission of mature foliage on both perennial and annual plant species. They are for instance quite active as defoliants on cotton, and defoliation properties have also been observed in other plant species such as roses, privet, apples, citrus, and brussel sprouts once the leaves have attained a mature state. Abscission of flowers and/or fruit following application of the phosphonic acid derivatives has been observed on a variety of plant species, including apples (*Malus domestica*), pears (*Pyrus communis*), cherries (*Prunus avium*), pecans (*Carva illinoensis*), grapes (*Vitis vinifera*), olives (*Olea europaea*), coffee (*Coffea arabica*) and snapbeans (*Phaseolus vulgaris*) - these abscission responses can be used to regulate flower production and as an aid in harvesting fruit.

6. Hastening Ripening and Color Promotion in Fruit:

The phosphonic acid derivatives have been shown to be capable of hastening the ripening of fruit (picked or unpicked) from a number of plant species, such as apples (*Malus domestica*), pears (*Pyrus communis*), cherries (*Prunus avium*), bananas and pineapples (*Ananas comosus*); and of removing the green color from harvestable fruit such as tomatoes (*Lycopersicon esculentum*) and regreened citrus such as oranges (*Citrus sinensis*) and lemons (*Citrus limon*).

7. Increasing Flowering and Fruiting:

Suitably applied, the phosphonic acid derivatives are capable of increasing flowering and fruiting in a number of economic crops, such as soybeans (*Glycine max.*), snapbeans (*Phaseolus vulgaris*), kidney beans (*Phaseolus vulgaris*) and zinnias (*Zinnia elegans*).

8. Abortion or Inhibition of Flowering and Seed Development:

Suitably applied, the phosphonic acid derivatives will inhibit flowering and/or abort seet development, for example in johnson grass (*Sorghum halepense*).

9. Prevention of Lodging:

Application of the phosphonic acid derivatives has been shown to induce rigor resulting in firmer and stronger plants capable of resisting natural tendencies towards lodging.This effect has been observed on a number of plant species, such as for example wheat (*Triticum aestivum*), barley (*Hordeum vulgare*), and pea (*Pisum sativum*).

10. Stimulation of Seed Germination and Breaking of Dormancy:

The phosphonic acid derivatives have been shown to stimulate the germination of for instance lettuce seed and to terminate the dormancy of tubers such as seed potatoes.

11. Resistance to Freeze Injury:

The phosphonic acid derivatives appear to increase the hardiness of various plant species, such as for example, lima beans (*Phaseolus vulgaris*).

12. Hormone or Epinasty Effects:

The phosphonic acid derivatives have been shown to produce hormone or epinasty effects upon various plants, including notably tomatoes (*Lycopersicon esculentum*).

13. Interactions with other Growth Regulators:

The phosphonic acid derivatives may of course be used in conjunction with other plant growth regulators, such as maleic hydrazide, N-dimethyl-amino-succinic acid, gibberellic acid and naphthalene acetic acid, and interact therewith producing synergistic or antagonistic responses in various plants.

14. Interactions with Herbicides:

While the phosphonic acid derivatives seem to have essentially no phtyo-toxic activity of their own, they may be used in their capacity as plant growth regulators in conjunction with herbicides, for instance with aminotriazole in the herbicidal control of johnson grass (*Sorghum halepense*).

15. Disease Resistance:

Disease resistance makes tissue resistant to invasion by plant pathogens by influencing the enzyme and plant processes which regulate growth nature disease immunity.

As previously stated, the phosphonic acid compounds usable in the practice of the present invention fall within the general formula:

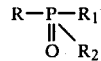

Specific phosphonic derivatives usable in the method for regulating plant growth falling within the scope of the present invention include:

1. The bis(acid chloride) of 2-chloroethyl-phosphonic acid.
2. The pyrocatechol cyclic ester of 2-chloroethyl-phosphonic acid.
3. The 4-chloropyrocatechol cyclic ester of 2-chloroethylphosphonic acid.
4. The mixed ethyl and 2-hydroxyphenyl diester of 2-chloroethyl-phosphonic acid.
5. The mixed butyl and 2-hydroxyphenyl diester of 2-chloroethyl-phosphonic acid.
6. The mixed propynyl and 2-hydroxyphenyl diester of 2-chloroethyl-phosphonic acid.
7. The 2-chloroethyl monoester of 2-chloroethyl-phosphonic acid.
8. 2-bromoethyl-phosphonic acid.

9. The bis(phenyl)-ester of 2-chloroethyl-phosphonic acid.
10. The tetrachloropyrocatechol cyclic ester of 2-chloroethyl-phosphonic acid.
11. 2-iodoethyl-phosphonic acid.
12. The saligen cyclic ester of 2-chloroethyl-phosphonic acid.
13. Salicyclic acid cyclic ester of 2-chloroethyl-phosphonic acid.
14. Phosphonoethyl-phosphonic acid.
15. Phosphonoethylthioethyl-phosphonic acid.
16. The 3-hydroxyphenyl monoester of 2-chloroethyl-phosphonic acid (which exists in polymeric form).
17. The bis(2-oxo-pyrrolidinylmethyl) ester of 2-chloroethyl-phosphonic acid.
18. The o-hydroxyphenyl monoester of 2-chloroethyl-phosphonic acid.
19. The mixed isopropyl and 2-hydroxyphenyl diester of 2-chloroethyl-phoshonic acid.
20. 2-fluoroethyl-phosphonic acid.
21. The mixed octyl and 2-hydroxyphenyl diester of 2-chloroethyl-phosphonic acid.
22. The mixed hexadecyl and 2-hydroxyphenyl diester of 2-chloroethyl-phosphonic acid.
23. The mixed tridecyl and 2-hydroxyphenyl diester of 2-chloroethyl-phosphonic acid.
24. The anhydride of 2-chloroethyl-phosphonic acid.
25. 2-chloroethyl-phosphonic acid.
26. 2-chloroethyl-butylester, 2-hydroxyphenylester of phosphonic acid.
27. 2-chloroethyl-2-chloroethylester of phosphonic acid.

Other useful phosphonic derivatives of this invention are salicyclic acid cyclic ester of phosphonamidic acid, the mixed phenyl and 2-hydroxyphenyl diester of 2-chloroethylphosphonic acid, 2-chloroethyl-dichlorophosphine, the bis (pentachlorophenyl) ester of 2-chloroethyl-phosphonic acid; 2-chloropropyl-phosphonic acid, 2-phenylthioethyl-phosphonic acid, the 2,3-pyridinedio cyclic ester of 2-chloroethylphosphonic acid, 2-chloroethyl-thiophosphonic acid (2-bromo, 2-fluoro and 2-iodo) and 2-chloroethyl-2,3-dibromo-4-hydroxy-2-butenyl ester polymer. Salts of the phosphonic derivatives of this invention may be used. Examples of such salts include the sodium, aluminum, zinc, potassium and lithium salts.

It is known that certain of the hereinabove mentioned phosphonic compounds will polymerize, but such compounds are usable to practice the present invention whether in monomeric or polymeric form so long as effective growth regulation is achieved.

The phosphonic derivatives used in the method of the present invention are soluble in varying degrees in water and so they can be applied to plants in aqueous solutions composed wholly or partially of water. Partial solutions include those formed of water and, for instance, acetone or methyl ethyl ketone. Any liquid medium may be used provided that it is not toxic to the plant. Where any particular derivative is less water-soluble, it may be solubilized by the use of co-solvents and the like. However, an example of a phosphonic derivative which can be applied in organic solution is the bis (acid-chloride) of 2-chloroethyl-phosphonic acid. Other media, including solids, like talc, will occur to those skilled in the art.

It will be seen from all of the foregoing that the plant growth regulating activity of the phosphonic acid derivatives of the present invention resides in the

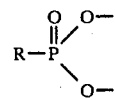

anion (assuming that the acidchloride and anhydride hydrolyze to form it). It is believed that any derivative of the aforesaid anion capable of releasing in, on or around the plant under treatment will display the desired plant - growth regulating activities. The phosphonic derivatives used in the practice of the present invention will include both compounds which hydrolyze very readily as well as compounds which hydrolyze only with difficulty, perhaps owing to steric hindrance.

Moreover, there are compounds which in the laboratory can be hydrolyzed only with difficulty, yet which apparently can be metabolized by the plant and hydrolyzed in its enzymatic systems quite readily.

The phosphonic acid derivatives employed in the practice of the present invention should normally be compounds known to be readily hydrolyzable, either in the laboratory or in the plant under treatment. The ability of any phosphonic derivative to be used in the practice of the present invention is initially determined in the greenhouse by testing such compound to determine their powers to produce epinasty in tomato plants, using the routine standard methods as set forth in the previously mentioned Bonner and Varner text.

It will be further seen that many of the phosphonic derivatives used in the practice of the present invention conform to the following general formula:

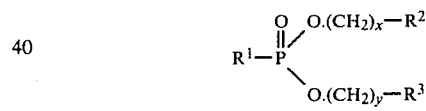

in which one of x or y is 0 and the other is 0 or 1; $R^1$ is haloethyl or phosphono-ethyl; $R^2$ is a hydrogen atom or a substituted or unsubstituted phenyl group; and $R^3$ is a hydrogen atom or a substituted or unsubstituted phenyl group or a halogen-substituted or unsubstituted, saturated or unsaturated hydrocarbon chain containing from 2 to 12 carbon atoms.

It can be seen from the foregoing that the dialkyl esters have been purposely excluded from the scope of compounds usable to practice the present invention because such dialkyl esters have not achieved any significant growth regulating results when used in the practice of the present invention. However, aryl diesters or even mixed alkyl and aryl diesters or even cyclo esters have proved to be effective in the growth regulating processes of the present invention.

It is preferred that the compounds falling within the scope of "R" in the general formula of compounds usable in the practice of the present invention be halo - ethyl, with 2-chloroethylphosphonic acid embodying the preferred compound. Of course, "R" can also be phosphono-ethyl as exemplified by a —PO(Y)Z group; wherein Y is a chlorine atom or an —$OR^4$ group; $R^4$ is a hydrogen atom or a salt-forming cation or a substituted or unsubstituted aryl, arylmethylene, heterocyclyl or heterocyclylmethylene group, or the X(CH$_2$)$_2$.PO(Z) group wherein Z is defined as (but not necessarily identical to) Y or Z is a substituted or unsubstituted, saturated or unsaturated hydrocarbon chain wherein R$^4$ and Z together form an —O—$\phi$—, —O.CH$_2$—$\phi$—, —CO.O—$\phi$— or —CO.NH—$\phi$— linkage, where $\phi$ represents a divalent, substituted or unsubstituted benzene or heterocyclic ring.

It is to be understood that the term "aryl" refers especially to monocyclic aryl groups, whether substituted or not, but may extend also to bicyclic and polycyclic aryl groups provided that they bear one or more substituents capable of imparting water-solubility to the compound as a whole, such as sulphonate groups.

The substituted or unsubstituted, saturated or unsaturated hydrocarbon chains present in the phosphonic derivatives usable in the practice of the present invention, will normally be lower alkyl or cyclo-alkyl groups, such as ethyl, isopropyl, butyl and cyclohexyl groups. The hydrocarbon grouping should range from to to 18 carbon atoms, since above 18 carbon atoms it has been found that the water-solubility of the compound as a whole decreases undesirably.

As will be demonstrated in connection with certain examples in this specification, compounds used in the process of the present invention have been quite effective in regulating plant growth and development in connection with a wide variety of plant species at various concentrations of active phosphonic acid compounds. Amounts of as little as 0.1 lb./acre of compounds falling under the generic definition of the formula:

have been observed to cause marked increase in branching and lateral growth of several varieties of tomato plants. Moreover, compounds used in the process of this invention, when employed at concentrations ranging from 0.1 lb. to 16 lbs./acre (or from 10 to 48,000 ppm) have demonstrated pronounced modifications in plant growth, including, but not limited to, increased fruiting and flowering and induction of sprouting as compared with similar untreated plants. The phosphonic derivatives may be stabilized against water or moisture incorporating an acid therein to insure that the pH is not greater than five, with the term "acid" being used to cover any material which will impart the desired pH value. Also, an appropriate buffering agent can be used to maintain the pH of the composition at five or less.

The precise amount of phosphonic acid compound will depend upon the particular plant species being treated. An amount of from about 0.1 lb. to as much as 25 to 30 lbs./acre of these compounds, when applied to plants, will result in varying plant responses depending upon the total amount of compound used, as well as the particular plant species which is being treated. Of course, the amount of phosphonic acid compound should be non-phytotoxic with respect to the plant being treated.

It is preferred that the compounds used in the process of the present invention be applied at rates of ½ to 4 lbs./acre in aqueous solution and that the application rate in terms of total volume varies from about 1 to 100 gallons per acre.

The phosphonic acid compounds used in the process of this invention are generally soluble in water. In instances where these compounds are not appreciably water soluble, it has been found that contact with water frequently causes sufficient hydrolysis to result in a soluble product thereby obviating the necessity of utilizing sophisticated formulations containing surfactants, dispersing agents, extenders, etc. However, if desired, the compounds used in the process of this invention may be absorbed onto solid carriers such as vermiculite, attaclay, talc and the like for application via agranular vehicle. Application of water thin solutions or solids is accomplished using conventional equipment that is well known in the art.

Although the preferred method of application of the compounds used in the process of this invention is directly to the foliage and stems of plants, it has been found that such compounds may be applied to the soil in which the plants are growing, and that such compounds will be root-absorbed to a sufficient extent so as to result in plant responses in accordance with the teachings of this invention.

The compounds used in the process of the present invention are preferably applied to growing plants as set forth in many of the examples in this specification. However, under certain circumstances, the compounds used in the process of the present invention are active in seed treatment, for instance, lettuce seeds and oat seeds.

Certain compounds which are usable in the process of the present invention may be prepared in accordance with said concurrently filed application Ser. No. 617,820 entitled "Phosphonic Acid Esters and the Method for Their Preparation", the entire disclosure of which is hereby incorporated by reference. The preparation techniques set forth in said copending application may be used to prepare other compounds falling within the scope of the present invention, and the preparation techniques of such compounds will readily occur to those skilled in the art. For instance, the preparation techniques of said copending application deal essentially with the situation in which R$_1$ is haloalkyl but it should be quite clear that the same techniques may be utilized with the starting materials containing the desired R$_1$ substituent.

As further set forth in said copending application, certain of the compounds falling within the scope of the present invention may be described as catechol or substituted catechol half esters of 2-haloethylphosphonic acid.

The hydrolysis of the cyclic ester, unlike hydrolysis of other phosphonate esters, proceeds rapidly at about room temperature with evolution of heat and consequently, there is no need to employ elevated temperatures, although temperatures up to about 60° C. may be employed. Temperatures higher than about 60° C. should be avoided since the phosphonic acid half esters of the invention hydrolyse at such temperatures.

The catechol cyclic esters employed as a starting material for producing the compounds used in the process of the invention may be prepared in accordance with the process disclosed by Kabachnik et al, Izvest, Akak Nauk SSSP, o.k.h.n. 1947, 97 (Chem. Abstracts 42, 4132e) both hereby incorporated by reference. Thus, as disclosed by Kabachnik et al, the starting materials for producing the compounds used in the process of the invention are produced by reacting a 2-haloethylphosphonyl chloride with catechol or a substituted catechol, e.g., 2-chloroethylphosphonyl chloride is heated with catechol at 150°-160° C. to produce the catechol cyclic ester of 2-chloroethylphosphonic acid. Similarly, a substituted catechol, for example, a halo catechol, produced by adding chlorine or bromine to an acetic acid solution of catechol, may be reacted with 2-chloroethylphosphonyl chloride to produce the corresponding cyclic ester. As a further alternative, the catechol cyclic ester of 2-chloroethylphosphonic acid may be treated to effect substitution thereof. Thus, for example, an O-dichlorobenzene solution of the catechol cyclic ester of 2-chloroethylphosphonic acid may be warmed with an excess of sulfonyl chloride to produce a tetrachloro substitute catechol cyclic ester of 2-chloroethylphosphonic acid.

The following examples are illustrative of methods of preparing compounds that are used in the process of the present invention.

EXAMPLE A 4.4 parts of the cyclic ester of pyrocatechol with 2-chloro-ethylphosphonic acid were added to 44 parts of water, with stirring at 27° C. An exothermic heat of hydrolysis was noted in a 3° temperature rise to 30° C. The slightly milky solution was heated briefly to 50° C. and water removed at this temperature in a slash evaporator at a vacuum of about 30 mm. 4.8 parts of the catechol half ester of 2-chloroethylphosphonic acid was recovered as a colorless liquid. The phosphonic acid half ester was soluble in water, had a titration curve typical of a strong monobasic acid and showed no tendency to hydrolyze in aqueous solutions at room temperature, even after standing for three weeks. The phosphonic acid half ester hydrolyzes rapidly in boiling water.

EXAMPLE B 3.4 parts of the cyclic ester of pyrocatechol with 2-chloro-ethylphosphonic acid were added to 0.28 part of water (the stoichiometric amount of water required for hydrolysis) at 30° C. and there was a temperature rise to 80° C. The mixture was cooled and 3.6 parts of the catechol half ester of 2-chloroethylphosphonic acid was recovered as a viscous liquid.

The above procedure is also employed to produce the catechol half ester of 2-bromoethylphosphonic acid.

In order to illustrate the surprising results flowing from this invention there are presented below a series of experimental test results which are presented solely by way of illustration and are in no way intended to be construed as in any way limiting the scope of this invention.

It has been theorized that with the practice of the present invention the phosphonic derivatives break down outside the plant while still in the aqueous solution in which they were applied, and that the ethylene thus released is assimilated by the plant in gaseous form. However, this seems unlikely since even when stabilized against hydrolytic breakdown, the phosphonic derivatives will to a greater or lesser extent exert plant growth regulating activity when applied to plants, as demonstrated for instance by the epinasty tests upon tomato plants.

It is therefore theorized that the phosphonic derivatives used in the practice of the present invention exert their growth regulating activity, at least in the great majority of cases, by assimilation into the metabolic system of the plant. Indeed, analytical investigations have shown that immediately following application to the plant, residues of these phosphonic derivatives are for a limited period of time to be found in plant tissues. Other investigations have shown that in many plants some time after the application of the phosphonic derivatives, the plant tissues contain detectable amounts of ethylene.

From the foregoing it can be concluded that the phosphonic derivatives are broken down within plant tissue to release ethylene, and that the ethylene thus released exerts its normal functions. One conclusion from this is that the ethylene causes the artificial acceleration of the plant's natural life cycle, but it seems that the present invention does more than this because the plant growth regulating effects of the present invention occur to a greater degree than in nature. Indeed, it appears that the amount of ethylene released within the plant tissue is greater than that which could be derived from the phosphonic derivatives assimilated by the plant tissues. If this is correct, then it would seem to follow that the assimilation of the phosphonic derivatives by the plant tissues may trigger-off the enzymatic or other systems within the plant which in themselves generate ethylene.

The foregoing explanation is presented in an effort to promote a better understanding of the present invention, but since other investigations are still being carried out, it is quite possible that additional observations may necessitate a revision or even an abandonment of such a theory. In recognition of this it is again repeated that the reasons why the present invention has proved to be so successful have not as yet been determined with certainty, and this specification is to be so understood.

There will now be presented a large number of examples which primarily involve 2-chloroethylphosphonic acid as applied under a variety of application rates and concentrations to a wide variety of plant, seed, vegetable and fruit species. The other thirty-three compounds specifically disclosed hereinabove have shown sufficiently positive results in tomato - epinasty tests as to warrant the conclusion that such compounds can be used in the practice of the present invention. The tomato plant - epinasty test is a very reliable indicator of ethylene response.

Thus, it can be said with reasonable certainty that a compound, such as the other thirty-three compounds specified hereinabove, would show a positive response in the tomato plant - epinasty test or also show plant growth regulating characteristics of one or more of the other fourteen categories set forth hereinabove.

The following examples are illustrative of the wide range of plant species that can be subjected to the plant growth regulating process of the present invention, using 2-chloroethylphosphonic acid, but in view of the fact that the other thirty-three compounds did show positive results in the tomato plant - epinasty test and as further confirmed in some additional examples set forth hereinafter, it has been concluded that all thirty-four phosphonic compounds as well as other compounds falling within the scope of the appended claims can be used in the practice of the present invention.

It is recognized that it is a virtually impossible task to try to test even 2-chloroethylphosphonic acid on every existing plant species. However, as will be seen from an evaluation of more than one hundred examples to follow, the Applicants have subjected 2-chloroethylphosphonic acid to tests involving an extremely wide variety of plant species. Nevertheless, there is no intention that the invention be limited to these compounds as in the future, workers in the art may find the process of the present invention to be an effective growth regulant on other plants.

However, it should readily occur to one skilled in the art that the recognition of improved results using the compounds of the present invention in connection with other plants, seeds, fruits and vegetables not specifically set forth herein is readily within the abilities of one skilled in the art.

EXAMPLE 1

This evaluation demonstrates the use of a compound of the invention for induction of flower abscission.

Tomato (Lycopersicon sp.) plants were sprayed with aqueous solutions of 2-chloroethylphosphonic acid during flowering. The results are recorded below.

| Treatment | % Flower abscission Days after treatment | |
|---|---|---|
| rate ppm | 7 | 14 |
| Control | 0 | 0 |
| 50 | 38 | 40 |
| 150 | 55 | 57 |
| 300 | 57 | 68 |
| 600 | 93 | 96 |
| 1000 | 100 | 100 |

Use of a compound of the invention was effective for inducing abscission of flower buds and flowers. Rates of 50 to 300 ppm of 2-chloroethylphosphonic acid were most effective in abscising unpollinated flowers whereas those not abscised were pollinated at the time of treatment. Rates of 600 and 1000 ppm abscised both pollinated and unpollinated flowers and buds. Treatment rates of 300 to 1000 ppm caused a temporary dwarfing of vegetative growth and leaf epinasty.

The control of flowering on tomatoes through flower abscission is of economic value in relation to concentration of harvest maturity. Elimination of early set flowers and late flower set will increase the number of ripe fruit in proportion to the amount of over-ripe fruit produced from early flower set and the percent of green fruit at harvest in relation to late flower set. This reduces the amount of sorting required to separate over-ripe and green fruit from desirable ripe fruit at harvest.

EXAMPLE 2

This evaluation demonstrates the use of a compound of the invention for inducing earlier flowering and increasing flower numbers.

Tomato (Lycopersicon sp.) plants were sprayed with aqueous solutions of 2-chloroethylphosphonic acid in the cotyledon to the first true leaf stage. The results are recorded below.

| Treatment rate | Number of open blossoms per plant - 4 weeks after treatment | Number of flowers 4 weeks after treatment |
|---|---|---|
| Control | 1 | 4 |
| 250 | 4 | 7 |
| 500 | 5 | 8 |
| 1000 | 6 | 9 |

Use of a compound of the invention to increase the number of flowers per plant and to increase early uniform blossom opening for fertilization is of economic value particularly in areas with a short growing season. Earlier flower pollination and uniform fruit set will result in earlier harvest maturity. Further, increased flower numbers offer the potential for increasing crop yield.

EXAMPLE 3

This evaluation demonstrates the use of a compound of the invention as a chemical ripening agent for acceleration and concentration of harvest maturity.

Tomato (Lycopersicon sp.) plants were treated with aqueous solutions of 2-chloroethylphosphonic acid prior to harvest. The results are recorded below.

| Treatment | % Yield of red ripe fruit Days after treatment | | | |
|---|---|---|---|---|
| rate ppm | 7 | 14 | 21 | 24 |
| Control | 35 | 53 | 71 | 83 |
| 250 | 51 | 69 | 87 | — |
| 500 | 64 | 82 | 89 | — |
| 1000 | 71 | 89 | — | — |
| 5000 | 72 | 90 | — | — |

Acceleration of harvest maturity was obtained with all treatments. Concentration of red ripe fruit is of economic value for increasing crop recovery of once-over mechanical harvesting or for a reduction in the number of harvesting times required to collect the tomato crop by hand picking.

Treatments of 1000 and 5000 ppm induced some defoliation. Defoliation is important in late production areas in order to provide exposure of the fruit to air and sunlight thereby reducing the incidence of disease and delayed ripening.

EXAMPLE 4

This evaluation demonstrates the use of a compound of the invention as a fruit ripening agent.

Tomato (Lycopersicon sp.) fruit were treated with aqueous solutions of 2-chloroethylphosphonic acid as a post-harvest spray or dip treatment to fruit which had been detached from the plant. The results are recorded below.

| Treatment | % Red ripe fruit in days after treatment | | | | | |
|---|---|---|---|---|---|---|
| rate ppm | 2 | 5 | 8 | 10 | 15 | 21 |
| Control | 0 | 0 | 0 | 3 | 50 | 80 |
| 500 | 0 | 0 | 10 | 50 | 84 | 100 |
| 1,000 | 5 | 40 | 65 | 85 | 100 | — |
| 5,000 | 20 | 63 | 100 | — | — | — |
| 10,000 | 29 | 74 | 100 | — | — | — |

Tomatoes ripened more rapidly and uniformly after treatment as a postharvest dip or spray with a compound of the invention. Very immature as well as mature green fruit were ripened. Significant color improvement was obtained in two days following treatment with 5000 and 10,000 ppm. Acceleration of ripening was in proportion to concentration of 2-chloroethylphosphonic acid and internal as well as external red color developed more quickly in treated fruit. Variability in red color from fruit to fruit during the ripening period was markedly reduced in treated fruit. The greatest acceleration of ripening was observed when immature green or mature green fruit were dipped in aqueous solutions of 2-chloroethylphosphonic acid for two minutes and held at a temperature of 70° F. Fruit which were pink or red in color were not accelerated to the same extent as immature or green mature fruit, however, uniformity of ripening and color development was increased.

Fruit ripening after treatment with a compound of the invention appears to be normal in every respect. Changes in color, pH, and firmness were similar to those occurring in untreated fruit, however, these changes occurred more rapidly and uniformly. Further, it appears that use of a compound of the invention as a chemical ripening agent will accelerate and induce the normal sequence of events occurring during ripening.

Treatment with a compound of the invention is of economic value particularly when tomatoes are harvested green in the Southern States during the winter and shipped North where they are held in ripening rooms until mature. Post-harvest treatment will reduce the time in storage and reduce costly sorting of tomatoes in ripening rooms as a result of better uniformity and acceleration of ripening. Treatment could be applied to detached fruit before shipment, with the fruit ripening enroute to market, thereby eliminating the need for ripening rooms.

EXAMPLE 5

This evaluation demonstrates the use of a compound of the invention for concentration of fruit maturity.

Tomato (Lycopersicon sp.) plants were sprayed with aqueous solutions of 2-chloroethylphosphonic acid two weeks prior to harvest. The results are recorded below.

| Treatment rate ppm | % Concentration of maturity by weight | | |
|---|---|---|---|
| | green | red ripe | over-ripe |
| Control | 37 | 50 | 13 |
| 500 | 25 | 62 | 11 |
| 1,000 | 18 | 71 | 11 |
| 5,000 | 5 | 85 | 10 |
| 10,000 | 3 | 87 | 10 |

As the concentration of 2-chloroethylphosphonic acid increased the proportion of green fruit decreased with a corresponding increase in red ripe fruit. The percentage of over-ripe fruit was unaffected. Rates of 5000 and 10,000 ppm caused some leaf chlorosis and epinasty of foliage but did not impair fruit appearance in any respect. Internal as well as external red color was increased in treated fruit.

Use of a compound of the invention in the field prior to harvest is of economic value particularly for mechanical once-over harvest technique since chemical treatment concentrates red ripe fruit maturity and thereby increases the proportion of ripe fruit recovered during a single harvest. Not only is the yield of usable red ripe fruit increased following a field application with a compound of the invention but there is also a saving in labor required to sort mechanically harvested green fruit. Treated fruit does not become over-ripe sooner than normal since the chemical accelerates green fruit to a greater extent than pink or red fruit following treatment.

EXAMPLE 6

This evaluation demonstrates the use of a compound of the invention for accelerating fruit maturity.

Tomato (Lycopersicon sp.) plants were sprayed with aqueous solutions of 2-chloroethylphosphonic acid at various intervals after pollination. The results are recorded below.

| Treatment rate ppm | Time of application in days after pollination | Days until fruit developed full red color |
|---|---|---|
| Control | — | 55 |
| 250 | 0 | 49 |
| 250 | 2 | 48 |
| 250 | 2, 9 & 16 | 40 |
| 250 | 39 | 47 |
| 500 | 0 | 48 |
| 500 | 2 | 47 |
| 500 | 14 | 46 |
| 500 | 39 | 46 |
| 1000 | 14 | 43 |
| 1000 | 39 | 46 |

All of the treatments with 2-chloroethylphosphonic acid accelerated early maturity as expressed by full red color development of treated fruit regardless whether the treatment was applied shortly after pollination or just prior to harvest. Treatment with 500 ppm at pollination and 2 days after pollination induced some fruit abscission and flower abscission. Treatments did not have any significant effect on ultimate fruit size but markedly accelerated maturation and ripening. Induction of early crop maturity is of economic value for marketing of fruit.

EXAMPLE 7

This evaluation demonstrates the use of a compound of the invention for inducing disease resistance.

Tomato (Lycopersicon sp.) plants were sprayed with aqueous solutions of 2-chloroethylphosphonic acid alone and with a fungicide just prior to harvest. The results are recorded below.

| Treatment rate | % Anthracnose disease for 2 tomato varieties | |
|---|---|---|
| | New Yorker | New York 903 |
| Control | 34.2 | 47.0 |
| 2-Chloroethylphosphonic acid @ 5000 ppm | 31.4 | 26.6 |
| 2-chloroethylphosphonic acid @ 5000 ppm + Fungicide (1) | 4.7 | 7.4 |
| Fungicide (1) | 8.8 | 14.5 |

(1) Difolatan 4F applied at 1.2 lbs active per acre

Use of a compound of the invention was effective for reducing the incidence of Anthracnose disease. Disease control was further increased when 2-chloroethylphosphonic acid was applied in conjunction with a fungicide such as Difolatan when compared to use of the fungicide alone.

EXAMPLE 8

This evaluation shows abscission effects in apple fruit. Apple trees (*Malus domestica;* variety McIntosh) were sprayed to run off with aqueous solutions of 2-chloroethylphosphonic acid just prior to normal fruit harvest. Fruit abscission noted seven and eleven days after treatment was as follows:

| Treatment | % Fruit abscission | | Maturity Index | |
|---|---|---|---|---|
| | 7 days | 11 days | lb/pressure | % maturity increase |
| Control (0 ppm.) | 17 | 38 | 6.9 | 0 |
| 500 ppm. | 66 | 100 | 4.6 | 34 |
| 1500 ppm. | 85 | 100 | 4.5 | 35 |

-continued

| Treatment | % Fruit abscission | | Maturity Index | |
|---|---|---|---|---|
| | 7 days | 11 days | lb/pressure | % maturity increase |
| 4500 ppm. | 89 | 100 | 4.0 | 42 |

The results show how early abscission is induced causing the fruit to drop off the tree (50% abscission, for example, equals 50% fruit drop) and enabling harvesting of the fruit to be effected earlier.

Abscission was accompanied by ripening (maturing) of the fruit, as seen by the maturity index results.

The maturity index, based on fruit pressure tests, is expressed as a decrease in apple firmness or softening of tissue, which indicates fruit maturity. The abscission and ripening acceleration demonstrates the effectiveness of the phosphonic derivatives in allowing earlier harvesting.

EXAMPLE 9

In another apple abscission Evaluation (*Malus domestica:* variety Rome Beauty) were sprayed with aqueous solutions of 2-chloroethylphosphonic acid, and the fruit then mechanically harvested 16 days later using a tree shaker (which will remove only those fruit which are loose). The following results were noted:

| Treatment | Rate (ppm) | % drop of fruit on tree before harvest | % fruit on tree removed by shaker |
|---|---|---|---|
| Control | — | 2.1 | 81.7 |
| 2-chloroethyl-phosphonic acid | 500 | 7.7 | 95.5 |
| 2-chloroethyl-phosphonic acid | 1000 | 22.0 | 98.8 |
| 2-chloroethyl-phosphonic acid | 2000 | 37.5 | 100 |

EXAMPLE 10

This evaluation again shows the increase in rate of harvesting of fruit on trees treated as opposed to trees untreated.

Apple trees (variety Gravenstein) were sprayed (when the fruit were beginning to mature) with aqueous solutions as specified below, and the trees and fruit were examined two weeks later. The following results were obtained:

| Treatment | Rate ppm. | Fruit drop % | Fruit firmness lb/sq. in. | Red colour % | Soluble solids % |
|---|---|---|---|---|---|
| Control | — | 5 | 14.3 | 90.8 | 11.8 |
| 2-chloroethyl phosphonic acid | — | 250 47.5 | 13.7 | 98.7 | 12.0 |
| 2-chloroethyl phosphonic acid NAA | 250 + 10 | 8 | 12.5 | 97.9 | 11.8 |

NAA — naphthalene acetic acid

It will be seen that the use of 2-chloroethyl-phosphonic acid stimulates both loosening and maturing of the fruit. The addition of NAA reversed the abscission promoting effect without interfering with the ripening process.

EXAMPLE 11

This evaluation also shows freeze damage resistance.

Apple seedlings (*Malus domestica*) variety Red Delicious, two weeks old were sprayed with an aqueous solution of 2-chloroethyl-phosphonic acid. Eighteen days later the plants were pre-cooled at +2° C. for one hour and then kept at −6° C. for 2 hours and thirty minutes. The frozen plants were then cultured and the following data recorded.

| Treatment | % Plants surviving freeze |
|---|---|
| Control | 0 |
| 200 ppm | 100 |

It is apparent from the results of the foregoing evaluations that the phosphonic derivatives of this invention are capable of imparting a wide variety of plant growth regulating responses.

EXAMPLE 12

This evaluation demonstrates the use of a compound of the invention as a growth regulator for accelerating fruit maturity and improving fruit color.

Apple (Malus sp.) variety Rome trees were sprayed just prior to normal harvest with aqueous solutions of 2-chloroethylphosphonic acid. Apples were also dipped in aqueous solutions of 2-chloroethylphosphonic acid after harvest. The results are recorded below.

| | Tree spray | | Fruit dip | |
|---|---|---|---|---|
| Treatment Rate | lbs Fruit firmness | % red color | lbs Fruit firmness | % red color |
| Control | 16.9 | 80 | 16.6 | 80 |
| 500 ppm | 15.2 | 95 | 14.7 | 94 |
| 1000 ppm | 14.3 | 92 | 13.9 | 96 |

As fruit matures to eatable quality the flesh softens. The reduction of fruit firmness on both pre and post harvest treated fruit demonstrates accelerated maturity. Red color was increased in both pre and post harvest treated fruit. Use of a compound of the invention is of value for inducing uniform desirable red color for marketing fruit and for accelerating eatable fruit maturity.

EXAMPLE 13

This evaluation demonstrates the use of a compound of the invention as a growth regulator for accelerating fruit maturity and improving fruit color.

Apple (Malus sp.) variety Golden Delicious trees were sprayed prior to harvest with aqueous solutions of 2-chloroethylphosphonic acid. Apples of the same variety were also dipped in aqueous solutions of 2-chloroethylphosphonic acid after harvest. The results are recorded below.

| | Tree spray | | Fruit dip | |
|---|---|---|---|---|
| Treatment Rate | lbs Fruit firmness | % Yellow color | lbs Fruit firmness | % Yellow color |
| Control | 17.2 | 50 | 16.9 | 45 |
| 500 | 15.3 | 90 | 15.2 | 91 |
| 1000 | 14.6 | 95 | 14.3 | 94 |
| 3000 | 14.0 | 98 | 13.7 | 97 |

As fruit matures to eatable quality the flesh softens. The reduction of fruit firmness on both pre and post harvest treated fruit demonstrates accelerated maturity. Further, use of a compound of the invention will remove green color from the fruit thereby increasing desirable yellow color expression when treated on the tree of after picking. Often genetically yellow apples remain quite green and fail to obtain full yellow color under various growing conditions. Pre or post harvest treatments will be of economic value for increasing the expression of yellow color for marketing yellow apple varieties.

EXAMPLE 14

This evaluation demonstrates the use of a compound of the invention as a growth regulator for control of fruit set.

Apple (malus sp.) trees were sprayed prior to bloom, at full bloom and at several intervals after full bloom (see table for state of development at different application times) with aqueous solutions of 2-chloroethylphosphonic acid. The results are recorded below.

| Treatment[1] rate ppm | Date applied | State of development | % Fruit[2] set | % Increase return bloom |
|---|---|---|---|---|
| 0 | May 1 | Delayed dormant | 36.2 | 0 |
| 200 | May 1 | Delayed dormant | 4.6 | 20 |
| 2000 | May 1 | Delayed dormant | 0 | 50 |
| 0 | May 17 | Pink | 31.4 | 0 |
| 200 | May 17 | Pink | 10.1 | 15 |
| 2000 | May 17 | Pink | 0 | 60 |
| 0 | May 23 | Full bloom | 28.3 | 0 |
| 1000 | May 23 | Flull bloom | 2.9 | 55 |
| 0 | June 2 | FB + 10 days | 28.0 | 0 |
| 50 | June 2 | FB + 10 days | 29.2 | 0 |
| 250 | June 2 | FB + 10 days | 10.6 | 20 |
| 300 | June 2 | FB + 10 days | 5.8 | 65 |
| 0 | July 6 | FB + 44 days | 31.7 | 0 |
| 75 | July 6 | FB + 44 days | 29.8 | 5 |
| 250 | July 6 | FB + 44 days | 33.6 | 5 |
| 1000 | July 6 | FB + 44 days | 1.6 | 10 |

[1]Mature trees with 4 replication branches on separate trees per treatment.
[2]Fruit per 100 blossom cluster as determined August 1.
FB = Full bloom Reducing fruit set during the current year is a common grower practice known as "thinning". Excellent "thinning" or reduction of fruit set was obtained following treatment with a compound of the invention when applied from the delayed dormant stage through 44 days after full-bloom. Compounds of the invention are also useful for increasing return bloom and fruit set the following year.

EXAMPLE 15

This evaluation demonstrates the use of a compound of the invention to induce freeze resistance.

Apricot (Prunus sp.) trees were sprayed with aqueous solutions of 2-chloroethylphosphonic acid. The results are recorded below.

| Treatment | % Fruit buds killed with - 11° F. |
|---|---|
| Control | 94 |
| 200 | 22 |
| 300 | 32 |
| 500 | 13 |

Freeze resistance of fruit buds and flowers will insure economic crop production on trees treated with a compound of this invention whereas untreated trees in this trial subjected to −11° F. will not have sufficient live fruit buds to produce an economic crop for the grower.

EXAMPLE 16

This evaluation demonstrates the use of a compound of the invention for stimulating shoot growth on rhizomes and increasing yield.

Asparagus (Asparagus sp.) rhizomes were sprayed and dipped in aqueous solutions of 2-chloroethylphosphonic acid. The results are recorded below.

| Treatment rate | % increase in shoots (spears) | % flower and fruit abscission |
|---|---|---|
| Control | 0 | 0 |
| 500 ppm | 10 | 75 |
| 1500 ppm | 25 | 100 |
| 4500 ppm | 52 | 100 |
| 9000 ppm | 27 | 100 |

Asparagus normally produces shoots or spears from rhizomes which must be harvested daily during the production period. With a compound of the invention, treatment of fall "ferns" (adult plant form), first emerging spring spears, or soil treatment of rhizomes would be of economic value for increasing yield by stimulating uniform spear emergence for a single harvest or reducing the number of daily harvests. Further, the ability of the asparagus plant to produce shoots may be increased by causing flower and fruit abscission on the female plant with a compound of the invention.

Elimination of summer fruit from the female plant removes the burden of maturing fruit enabling the plant to accumulate food reserves in the rhizomes for increased shoot production the following spring.

EXAMPLE 17

This evaluation demonstrates the use of a compound of the invention as a fruit ripening agent.

Avacado (Persea sp.) trees were sprayed with aqueous solutions of 2-chloroethylphosphonic acid just prior to normal harvest. Unripe fruits were also removed from the tree and dipped in aqueous solutions of 2-chloroethylphosphonic acid for one minute. The results are recorded below.

| Treatment rate ppm | % Ripe fruit 7 days after treatment | |
|---|---|---|
| | Preharvest spray | Postharvest dip |
| Control | 0 | 3 |
| 250 | 20 | 27 |
| 500 | 73 | 82 |
| 1000 | 100 | 100 |
| 5000 | — | 100 |

Treatment with a compound of the invention accelerated fruit ripening of avacadoes when applied as a preharvest spray or as a postharvest solution dip.

EXAMPLE 18

In another "branching" evaluation an aqueous solution of 2-chloroethylphosphonic acid was sprayed to run-off on azalea plants.

Two months later the plants were inspected and the following noted.

| Treatment rate | Observation |
|---|---|
| 1 kg/ha | Bud formation was stimulated and there were many lateral shoots |
| 2 kg/ha | Very many lateral shoots |

| Treatment rate | Observation |
|---|---|
| | close to plant top |

Evaluations performed using lower rates gave good flower induction.

EXAMPLE 18-A

This evaluation shows use of a compound of the invention to ripen bananas by stimulating metabolic processes associated with ripening.

Cut banana stalks bearing fruit were artificially ripened by being dipped in aqueous solutions of 2-chloroethylphosphonic acid at concentrations ranging from 100 to 4500 ppm. This effect, which presumably results from the destruction of chlorophyll and stimulation of carotenoid development, is of economic importance as unripe fruit are imported into European and Scandinavian countries and then artificially ripened before distribution.

EXAMPLE 19

This evaluation demonstrates the use of a compound of the invention to increase stem formation (tillering) and reduce overall stem height. Summer barley (variety Impala) was sprayed with aqueous solutions of 2-chloroethylphosphonic acid, with or without urea, at the 1½-2 leaf stage and the plants inspected some 10 weeks later. The following results were obtained, from which it will be seen that the compound of this invention-either alone or with the urea-decreased the total plant height (thus decreasing any tendency towards lodging) while increasing the average number of stems per plant (thus increasing potential crop yield).

| Treatment (s) | | Rate Kg/Ha | Stem height (cm) | Stem average plant |
|---|---|---|---|---|
| Control | | — | 93 | 3.2 |
| 2-chloroethyl-phosphonic acid | — | 2 | 87 | 3.4 |
| — | urea | 35 | 93 | 3.2 |
| 2-chloroethyl-phosphonic acid | urea | 2 + 35 | 84 | 3.8 |
| 2-chloroethyl-phosphonic acid | — | 4 | 81 | 4.5 |
| 2-chloroethyl-phosphonic acid | urea | 4 + 35 | 79 | 4.3 |

EXAMPLE 20

This evaluation demonstrates the use of a compound of this invention to increase crop yield. It shows that compounds of the invention can increase the fruit number and the weight of the aerial parts of *Phaseolus vulgaris* (varieties snapbean and kidney bean) when applied in aqueous solution at the first trifoliate stage at the rate of 1.12 kg/ha.

| Compound of the invention | Plant variety | Results (60 days after treatment) | |
|---|---|---|---|
| | | Pods/plant | Plant Weight (grams) |
| pyrocatechol cyclic ester of 2-chloroethyl-phosphonic acid | Snapbean Control treated | 6 15 | 29 70 |
| 2-chloroethyl-phosphonic acid | Kidney bean Control | 20 | 83 |
| | treated | 25 | 134 |

In this evaluation the treated plants were also shorter, with heavier stems, and had appreciably more lateral shoots than the controls. The effects are desirable, in that they reduce lodging and give greater crop bearing vegetation respectively.

EXAMPLE 21

This evaluation also demonstrates the use of a compound of the invention to increase crop yield.

French beans, variety Dwarf bean ("The Prince"), were treated with aqueous solutions of 2-chloroethyl-phosphonic acid at a rate of 0.5 kg/ha at the 1½-2 true-leaf stage. The crop was harvested twice and, as the following results show, an increase in yield per plant over that of the control plants was noted at the second harvest.

| Treatment | Average yield per plant (gms) at 2nd harvest |
|---|---|
| Control (0) | 6 |
| 2-chloroethyl-phosphonic acid | 27 |

EXAMPLE 22

This evaluation demonstrates the use of a compound of the invention to impart freeze damage resistance.

Seedling beans (*Phaseolus vulgaris*); variety Blue Lake, 2½ weeks old, were sprayed with aqueous solutions of 2-chloroethylphosphonic acid. Eleven days later the plants were pre-cooled at +2° C. for one hour and then kept at −5½° C. for 2 hours and twenty minutes. The frozen plants were then cultured in a greenhouse and the following data was recorded.

| Treatment | % Plants surviving freeze |
|---|---|
| Control (0) | 0 |
| 200 ppm | 100 - no damage |
| 2000 ppm | 100 - no damage |

EXAMPLE 23

French beans variety Dwarf bean "the Prince" were treated with aqueous solutions of 2-chloroethylphosphonic acid at the rates indicated at the 1½-2 true leaf flower bud stage. The following increases in total yield were noted.

| Treatment | Total yield per plant (gms) |
|---|---|
| Control | 41 |
| 0.25 | 46 |
| 0.50 | 48 |

EXAMPLE 24

This evaluation demonstrates the use of a compound of the invention as a growth regulator for inducing fruit abscission as an aid to harvest of mature fruit.

Black currants (Ribes sp.) shrubs were sprayed prior to harvest with aqueous solutions of 2-chlorethylphosphonic acid. The results are recorded below.

| Treatment rate ppm | % Fruit abscission following a hand shake |
| --- | --- |
| Control | 3 |
| 500 | 89 |
| 2000 | 91 |
| 5000 | 91 |

Treatments loosened currants on the shrub and as a result of weakening the link between the stem and the fruit, black currant fruit was easily removed following a hand shake of the plant. Treatment rates of 2000 and 5000 ppm also induced leaf defoliation.

Further, fruit samples collected from treated bushes contained no green berries indicating uniform stimulation of ripening had occurred when treated with a compound of the invention.

Stimulating fruit abscission with a compound of the invention will be of economic value for crop harvest by reducing the labor and time required to pick the fruit.

EXAMPLE 25

This evaluation demonstrates the use of a compound of the invention as a growth regulator for inducing fruit abscission and increasing ripe fruit recovery.

Blueberry (*Vaccinium corymbosum* and *Vaccinium angustifolium*) bushes were sprayed with aqueous solutions of 2-chloroethylphosphonic acid just prior to harvest. The results are recorded below.

| Treatment rate ppm | % Fruit abscission following a hand shake | % ripe fruit |
| --- | --- | --- |
| Control | 20 | 55 |
| 500 | 86 | 78 |
| 2000 | 95 | 85 |
| 5000 | 97 | 85 |

Treatments loosened blueberries on the bush and as a result of weakening the link between the stem and the fruit, blueberry fruit was easily removed following a hand shake of the plant. Treatment rates of 2000 and 5000 ppm also induced slight leaf defoliation.

Further, fruit samples collected from treated bushes contained no green berries indicating uniform stimulation of ripening had occurred when treated with a compound of the invention.

Stimulating fruit abscission with a compound of the invention will be of economic value for crop harvest as a result of increased crop recovery and ease of fruit removal.

EXAMPLE 26

This evaluation demonstrates the use of a compound of the invention to increase yields and reduce plant height.

Soybean (*Glycine max*) plants were sprayed at the 9-12 trifoliolate leaf stage with aqueous solutions of 2-chloroethylphosphonic acid. The results are recorded below.

| Treatment Rate lb/A | % Yield | % Height inhibition |
| --- | --- | --- |
| Control | 100 | 0 |
| 0.5 | 152 | 23 |
| 1.0 | 119 | 14 |

The term % height inhibition is a measure of reduction in stem height. The shorter plant showed less lodging.

EXAMPLE 27

20 ml portions of 2-chloroethylphosphonic acid in aqueous solution were applied at rates of up to 10,000 ppm to ornamental plants of the Bromiliadaceae family, and increases in flower induction were observed.

EXAMPLE 28

This evaluation demonstrates the use of a compound of the invention to induce freeze resistance.

Cherry (*Prunus* sp.) trees were sprayed with aqueous solutions of 2-chloroethylphosphonic acid. The results are recorded below.

| Treatment rate ppm | % Fruit buds killed with −11° F. freeze four months after treatment on variety | | | |
| --- | --- | --- | --- | --- |
| | BING | CHINOOK | RAINIER | AVERAGE |
| Control | 31 | 14 | 31 | 25 |
| 300 | 5 | 2 | 12 | 6 |
| 500 | 6 | 3 | 10 | 6 |
| 1,000 | 8 | 2 | — | 5 |
| 2,000 | 0 | — | 4 | 2 |

Protection of fruit buds and subsequent flowers from freeze damage is economically valuable to the grower to insure annual crop production.

EXAMPLE 29

This evaluation demonstrates the use of a compound of the invention to increase yield and reduce lodging.

Corn (*Zea* sp.) plants were sprayed with aqueous solutions of 2-chloroethylphosphonic acid prior to tasseling.

| Treatment Rate lb/A | % Yield | Ave. number of kernels per ear | % Lodging |
| --- | --- | --- | --- |
| Control | 100 | 579 | 27 |
| 2.0 | 102 | 554 | 13 |

These results show that an increase in yield was obtained with fewer kernels per ear indicating an increase in kernel size following treatment with a compound of this invention. Treatment also reduced lodging and increased the number of above-ground brace roots.

EXAMPLE 30

This evaluation demonstrates the use of a compound of the invention to control growth.

Corn (*Zea* sp.) plants were sprayed at the eight-leaf stage with aqueous solutions of 2-chloroethylphosphonic acid. The results are recorded below.

| Treatment rate ppm | 3 Months after application % height reduction | Increase in number of brace roots reaching soil surface |
| --- | --- | --- |
| Control | 0 | — |

-continued

| Treatment rate lb/A | 3 Months after application % height reduction | Increase in number of brace roots reaching soil surface |
|---|---|---|
| 0.25 | 13 | 0 |
| 0.50 | 14 | 1 |
| 1.0 | 17 | 3 |
| 2.0 | 23 | 3 |
| 4.0 | 39 | 4 |

Distance of ear from the soil surface to the ear tip was reduced with all treatments. Organ primordia (tissue in the stem which develops into roots, leaves or fruit) was stimulated as evidenced by increased numbers of brace roots from the stem reaching the soil surface.

EXAMPLE 31

This evaluation demonstrates the use of a compound of the invention as a growth regulator in connection with coffee.

Coffee (*Coffea arabica*) was sprayed preharvest with aqueous solutions of 2-chloroethylphosphonic acid, postharvest applications as an aqueous spray or solution dip were also applied. Results are recorded below.

| Treatment rate | Preharvest spray % increase in abscission | | | Preharvest and Postharvest % increase in ripe berries |
|---|---|---|---|---|
| | flowers | fruit | leaves | |
| Control | 0 | 0 | 0 | 0 |
| 400 ppm | 35 | 20 | 0 | 20 |
| 600 ppm | 60 | 60 | 5 | 35 |
| 800 ppm | 75 | 75 | 10 | 50 |
| 1200 ppm | 97 | 90 | 30 | 70 |
| 4000 ppm | 100 | 100 | 85 | 90 |

Both pre and post harvest treatments with a compound of this invention were effective for increased ripening and reducing the number of immature green berries. Timely applications of the compounds of this invention to flowers, fruit and leaves on the tree will induce abscission.

In many parts of the world coffee has a distinct number of flowerings spread over a number of weeks. The flowering is often closely related to periods of moisture. Since different flowerings ripen at different times, a number of selected fruit pickings are required. Further, fruit set from premature flowering is often lost to drought which lowers plant vigor as a result of supporting fruit which abort before maturity. By use of a growth regulator of this invention it will be possible to remove unwanted flowers thereby controlling harvest period and reducing the number of pickings required to harvest the crop. In addition application of a chemical of this invention will induce fruit abscission or decrease the pull-force required to remove the coffee from the tree. This effect should be of economic value to the development of mechanical harvesting techniques. Further, treatment of the fruit both pre and postharvest will accelerate maturity as evidenced by the increased number of red berries.

EXAMPLE 32

This evaluation demonstrates the use of a compound of the invention to increase crop yield and reduce plant height.

Cotton plants (*Gossypium hirsutum*) were sprayed, when squares (the bolls) were just forming, with aqueous solutions of 2-chloroethylphosphonic acid. The following results were recorded ten weeks later.

| Treatment Rate kg/Ha | Bolls/Plant | Change in plant height |
|---|---|---|
| Control (0) | 19.1 | — |
| 1.12 | 29.3 | +2% |
| 2.24 | 24.7 | −12% |
| 4.48 | 26.0 | −13% |

This increased yield of cotton is apparent. The reduction in plant height is useful, being indicative of a general reduction of non-useful vegetation.

EXAMPLE 33

This evaluation demonstrates use to give increased branching.

Ornamental shrubs were sprayed to run off with aqueous solutions of 2-chloroethylphosphonic acid and the plants were inspected 3 months later and the following noted:

| Shrub | Treatment | Branch (no.) | Height (cm) |
|---|---|---|---|
| Chrysanthemum (variety Gipsy) | Control (0) | — | 100 |
| | 100 ppm | 2 | 97 |
| | 500 ppm | 3 | 87 |
| | 1000 ppm | 20 | 38 |
| Carnation (pink) | Control (0) | 4 | 20 |
| | 100 ppm | 5 | 25 |
| | 1000 ppm | 7 | 38 |
| Fuchsia | Control (0) | 21 | 21 |
| | 100 ppm | 33 | 23 |
| | 1000 ppm | 31 | 26 |

It will be seen that in general the treated plants were more highly branched than the control plants, thus giving more potential flower sites. It will also be seen that the chrysanthemum plants' heights were reduced.

EXAMPLE 34

This evaluation demonstrates the use of a compound of the invention to induce leaf abscission.

Cotton (Gossypium sp.) plants were sprayed just prior to mature boll harvest with aqueous solutions of 2-chloroethylphosphonic acid. The results are recorded below.

| Treatment rate ppm | % Defoliation 10 days after treatment |
|---|---|
| 5,000 | 9 |
| 10,000 | 35 |
| 20,000 | 85 |
| 40,000 | 97 |

Abscission (means "falling-off" or being freed from the plant) is of economic benefit in cotton for machine harvesting efficiency. Leaf removal reduces green stain of cotton lint, permits earlier harvest, reduces boll rot, removes leaf insect problems and reduces lodging.

EXAMPLE 35

This evaluation demonstrates the use of a compound of the invention for accelerating fruit maturity and reducing fruit pull-force at harvest.

Cherry (*Prunus avium* and P. Cerasus) trees were sprayed with aqueous solutions of 2-chloroethylphosphonic acid. The results are recorded below.

| Treatment rate | Fruit removal force in grams | Soluble solids % | % increase red color |
|---|---|---|---|
| Control | 350 | 13.6 | 0 |
| 250 ppm | 250 | 15.5 | 20 |
| 500 ppm | 210 | 15.6 | 21 |
| 1000 ppm | 155 | 16.9 | 30 |
| 2000 ppm | 80 | 16.4 | 37 |

Use of a compound of the invention will lower the pull-force of the fruit making it easier to pick. The link between the fruit and the stem is weakened and upon picking the fruit is separated from the stem. Separation of fruit from the stem is economically valuable since it reduces sorting and stem removal during processing. It is understood, however, that this effect would not be desirable for cherries which are processed with the stems attached. Treatment with 1000 and 2000 ppm caused sap flow, gum, to extrude from lenticils of treated twigs; leaf abscission was also recorded.

Acceleration of harvest maturity is apparent by the increase in red color expression and the increase in soluble solids. A spaced acceleration of fruit maturity, time-controlled by a compound of the invention will also be of economic value for extending the normal harvest period.

EXAMPLE 36

This evaluation demonstrates the use of a compound of the invention as a growth regulator for improving the harvest efficiency of fruit.

Cherry (*Prunus aveum* and Prunus Cerasus) trees were sprayed preharvest with aqueous solutions of 2-chloroethylphosphonic acid. The results are recorded below.

| Treatment rate ppm | Fruit removal force in grams | Ave time to harvest (seconds) | % Removed without stems |
|---|---|---|---|
| Control | 352 | 28.7 | 50 |
| 250 | 273 | 11.5 | 90 |
| 500 | 237 | 10.5 | 95 |

The reduction in fruit removal force following use of a compound of the invention is reflected in easier harvest. The harvest time was reduced 60% on treated trees.

Further, the reduction in shaking time required for harvesting a tree or a reduction in machine shaking force that is required to remove the fruit will lower the danger of tree injury and reduce fruit bruising. Reducing fruit removal force will increase the percentage of total crop removed.

The link between the fruit and the stem is weakened and when machine harvested or hand picked a high percentage of fruits on treated trees are removed without stems. Use of a compound of the invention results in a smoother separation of the fruit from the stem with a reduction in the proportion of fruits with torn flesh at the point of separation. This smooth separation of stem and fruit without tearing the skin is of importance in quality maintenance through postharvest handling operations of both sweet and tart cherries.

The trend is toward increased use of machines to mechanically harvest fruit. This fruit is often difficult to remove, however, use of a compound of the invention to hasten or promote the abscission process is of economic value to aid and improve harvest efficiency.

EXAMPLE 37

Cucumber plants were sprayed with an aqueous solution of 2-chloroethylphosphonic acid at the 1–3 true leaf stage. They were then inspected at the 13-true leaf stage, and the following noted.

| Rate (ppm) | No. female flowers |
|---|---|
| 0 | 2–3 |
| 62 | 13 |
| 250 | 13 |

The increase in flowers is to be noted at the low rates of treatment.

EXAMPLE 38

This evaluation demonstrates the use of a compound of the invention for control of vegetative growth and color promotion.

Cranberries (*Vaccinium oxycroccus*) plants were sprayed just prior to vegetative shoot production in the early spring with aqueous solutions of 2-chloroethylphosphonic acid. Aqueous solutions of 2-chloroethylphosphonic acid were also applied just prior to harvest and as a postharvest solution dip to fruit which had been picked. The results are recorded below.

| Treatment rate ppm | % Growth inhibition Spring treatment | % Increase red color Preharvest | % Increase red color Postharvest |
|---|---|---|---|
| Control | 0 | 0 | 0 |
| 500 | 10 | 30 | 35 |
| 5,000 | 30 | 50 | 48 |
| 10,000 | 50 | 65 | 68 |

Vegetative shoots which develop after spring treatment with a compound of the invention had shorter internodes and were shorter in length when compared to untreated plants. Terminal runner growth was inhibited ten to fifty percent. This inhibition is of economic value for slowing down the normal excessive vegetation often produced in bog production. When excessive vegetative growth occurs, fruit set and yield are generally reduced the following year.

Treatment of cranberries prior to harvest or after picking with a compound of the invention increased the percent and uniformity of red color expressed by the fruit. Induction of fruit abscission was also recorded with a preharvest treatment of 10,000 ppm.

Color enhancement in fruit is an economic factor in fruit quality determinations.

EXAMPLE 38-A

This evaluation demonstrates the use of a compound of the invention for control of sex expression in cucurbits.

Cucumber (Cucumis sp.) plants were sprayed with aqueous solutions of 2-chloroethylphosphonic acid when plants were in the first to fifth true leaf stage of vegetative development. The results are recorded below.

| Cultivar and normal sex expression | Treatment rate ppm | Node of 1st floral bud | | Node of first nonaborted flower | |
|---|---|---|---|---|---|
| | | Male | Female or perfect | Male | Female or perfect |
| Wisconsin SMR 18 (monoecious) | 0 | 1.0 | 4.0 | 3.5 | 4.0 |
| | 250 | 19.5 | 1.0 | 19.5 | 4.5 |
| | 500 | ** | 1.0 | ** | 5.0 |
| MSU 713-5 (gynoecious) | 0 | ** | 1.0 | ** | 2.0 |
| | 250 | ** | 1.0 | ** | 4.5 |
| | 500 | ** | 1.0 | ** | 5.0 |
| Lemon (andromonoecious) | 0 | 1.0 | 13.5 | 1.0 | 13.5 |
| | 250 | 15.0 | 1.0 | 15.0 | 4.0 |
| | 500 | ** | 1.0 | ** | 4.5 |

**No male flowers produced at the first 20 nodes

Most cucumber cultivars are monoecious which is a term meaning that one or more male flowers develop on the first few nodes followed by an occasional female flower developing at later nodes. The monoecious cultivar treated with 2-chloroethylphosphonic acid produced several female but no male flowers at each of the first eighteen nodes on the main stem, while untreated plants had several male flowers at each of these nodes.

Gynoecious cucumbers which normally produce female flowers except under environmental stress were not modified by chemical treatment since control as well as treated plants produced only female flowers.

The andromonoecious cultivar which normally develops many nodes with only male flowers on the main stem before producing single perfect flowers as well as several male flowers on some of the later nodes responded to chemical treatment of 2-chloroethylphosphonic acid by producing several perfect or female flowers but no male flowers at each of the first fourteen nodes on the main stem.

The flower buds at the first three nodes of treated plants of each cultivar aborted before fertilization, however, flowers at subsequent nodes were normal and did not abort after fertilization.

Early induction of female flowers is of economic value for increasing fruit yields through early fruit set by female flowers.

EXAMPLE 39

This evaluation demonstrates the use of a compound of the invention for inducing disease resistance.

Mildew-susceptible cucumber (Cucurbits sp.) plants were sprayed with aqueous solutions of 2-chloroethylphosphonic acid. The results are recorded below.

| Treatment Rate | % plants with mildew disease | % leaf area infected |
|---|---|---|
| Control | 100 | 100 |
| 100 ppm | 20 | 5 |
| 250 ppm | 5 | 1 |
| 500 ppm | 0 | 0 |

Use of a compound of the invention is unique for inducing disease resistance since it influences the enzyme and plant processes which regulate growth and natural disease immunity. There is an association between increased peroxidase activity and genetic resistance to plants diseases such as powdery mildew (Erysiphe sp.). Disease resistance may be due to stimulation of polyphenolic compounds that are reduced while manganese is oxidized by a peroxidase-catalyzed reaction.

EXAMPLE 39-A

This evaluation demonstrates the use of a compound of the invention for regulation of sex expression in monoecious plants.

Cucumber (Cucumis sp.) plants of the monoecious variety Wisconsin SMR 18 were sprayed with aqueous solution of 2-chloroethylphosphonic acid at different stages of development of vegetative growth. Seed treatments were also made by immersing seeds in 2-chloroethylphosphonic acid for two hours before planting. The results are recorded below.

| Stage treated | Treatment ppm | Node of first floral bud | | Node of first nonaborted flower | |
|---|---|---|---|---|---|
| | | male | female | male | female |
| Control | 0 | 1.0 ± 0.0 | 5.6 ± 0.4 | 1.8 ± 0.2 | 5.6 ± 0.4 |
| Seed | 500 | 1.0 ± 0.0 | 6.0 ± 0.3 | 1.6 ± 0.2 | 6.0 ± 0.3 |
| | 1,000 | 1.0 ± 0.0 | 7.3 ± 0.2 | 1.7 ± 0.2 | 7.3 ± 0.3 |
| | 2,000 | 1.0 ± 0.0 | 6.8 ± 0.3 | 1.8 ± 0.2 | 6.8 ± 0.3 |
| Cotyledon | 125 | 3.0 ± 0.4 | 1.0 ± 0.0 | 3.0 ± 0.4 | 2.0 ± 0.4 |
| | 250 | 5.2 ± 0.7 | 1.0 ± 0.0 | 5.2 ± 0.7 | 1.7 ± 0.3 |
| | 500 | 9.0 ± 0.3 | 1.0 ± 0.0 | 9.0 ± 0.3 | 2.6 ± 0.4 |
| 1st leaf | 125 | 10.0 ± 0.4 | 1.0 ± 0.0 | 10.0 ± 0.4 | 1.6 ± 0.2 |
| | 250 | * | 1.0 ± 0.0 | * | 3.0 ± 0.4 |
| | 500 | * | 1.0 ± 0.0 | * | 11.0 ± 0.5 |
| 3rd leaf | 125 | 1.0 ± 0.0 | 3.0 ± 0.5 | 2.5 ± 0.4 | 6.5 ± 0.4 |
| | 250 | * | 1.0 ± 0.0 | * | 6.5 ± 0.7 |
| | 500 | * | 1.0 + 0.0 | * | ** |

*No male floral buds produced at the first 10 nodes.
**All female flowers at the first 10 nodes aborted before anthesis.

Immersion of seeds in 2-chloroethylphosphonic acid for two hours before planting had no effect on sex expression, however, foliage applications in the cotyledon stage or later resulted in shortened internodes and earlier development of female floral buds. Application of 2-chloroethylphosphonic acid in the tree-leaf stage modified sex expression at the cotyledonary node even though floral initiation and differentiation at this node should have been completed at the time of treatment indicating that the chemical inhibited development of the stamen and stimulated pistil development.

Female flower induction with a compound of the invention was not limited to those flowers differentiated at the time of treatment. A single application had very persistent effects and influenced sex expression of flowers that were not yet initiated at the time of treatment.

The regulation of sex expression and growth habit of cucumber plants has important potential applications. Fruit set early will increase yield potential. Use of a compound of the invention has value for hybrid seed production which can be accomplished by treating the monoecious maternal parent to inhibit its formation of male flowers thereby eliminating or reducing normal hand removal of male flowers.

Further, the problem of fruit setting too close to the base of the plant to permit multiple mechanical harvests can be overcome by the aborting of the first flowers by treatment with a compound of the invention.

EXAMPLE 40

This evaluation demonstrates the use of a compound of the invention for regulation of sex expression and control of vegetative growth.

Cucumber (Cucumis sp.) varieties Wisconsin SMR 18 (monoecious) and variety Lemon (andromonecious)

were sprayed with aqueous solutions of 2-chloroethylphosphonic acid and gibberellic acid at the first to third true leaf stage of vegetative development. The results are recorded below.

| Treatment | Rate ppm | Length of first internode (cm) | Node of first flower Female or perfect | Node of first flower Male | Number of flowers on first 10 nodes Female or perfect | Number of flowers on first 10 nodes Male |
|---|---|---|---|---|---|---|
| WISCONSIN SMR 18 | | | | | | |
| Control | 0 | 7.7 ± 0.6 | 8.0 ± 0.5 | 2.0 ± 0.0 | 2.0 ± 0.0 | 33.4 ± 1. |
| Gibberellic acid | 2000 | 16.0 ± 0.7 | ** | 1.3 ± 0.3 | 0.0 | 33.0 ± 4. |
| 2-chloroethylphosphonic acid | 250 | 3.7 ± 0.2 | 2.0 ± 0.0 | 14.3 ± 0.5 | 14.0 ± 1.7 | 0.0 |
| Gibberellic acid + 2-chloroethylphosphonic acid | 2000 +250 | 10.9 ± 0.6 | 3.0 ± 0.5 | 7.0 ± 0.5 | 4.0 ± 0.5 | 8.3 ± 2. |
| LEMON | | | | | | |
| Control | 0 | 4.6 ± 0.5 | ** | 3.0 ± 0.0 | 0.0 | 26.6 ± 0.3 |
| Gibberellic acid | 2000 | 8.3 ± 0.3 | ** | 5.7 ± 0.7 | 0.0 | 18.0 ± 1.6 |
| 2-chloroethylphosphonic acid | 250 | 3.0 ± 0.2 | 8.0 ± 0.5 | 11.7 ± 1.9 | 4.0 ± 0.8 | 2.3 ± 4.1 |

Number of plants for internode length measurements 12 days after treatment.
Data on sex expression were obtained on 3 plants 36 days after each treatment.
**No female or perfect flowers on first 17 nodes.

Application of 2-chloroethylphosphonic acid increased the number of female flowers produced and induced expression of female flowers earlier than on untreated plants. Use of a compound of the invention has anti-gibberellin activity. For example, the influence of 2-chloroethylphosphonic acid on sex expression and growth could be explained on the basis of this anti-gibberellin activity. Gibberellic acid antagonizes the response of cucumbers with respect to female flower induction caused by 2-chloroethylphosphonic acid. Further, the effects of 2-chlorophosphonic acid on vegetative growth inhibition were also antagonized by gibberellic acid. Giberellic acid is known to stimulate male sex expression and stimulate vegetative growth.

The use of 2-chloroethylphosphonic acid to increase the number of female flowers produced early in the vegetative growth period can be utilized to increase the amount of fruit ripe at the same time, thereby improving adaption to mechanical harvest. Vegetative growth inhibition as evidenced by shortening of the internodes will allow closer spacing and higher populations and consequently higher yields per acre.

EXAMPLE 41

This evaluation demonstrates the use of a compound of the invention for regulation of sex expression.

Cucumber (*Cucumis angilicus*) plants were treated with aqueous solutions of 2-chloroethylphosphonic acid at various growth stages. The results are recorded below.

| Treatment rate | % Male flowers produced in 25 nodes | | | |
|---|---|---|---|---|
| | 1-3 leaf | 3-5 leaf | 5-8 leaf | 1-3 + 3-5 + 5-8 leaf |
| Control | 85 | 85 | 85 | 85 |
| 25 | 30 | 32 | 36 | 30 |
| 50 | 10 | 14 | 16 | 8 |
| 125 | 0 | 4 | 6 | 0 |
| 250 | 0 | 2 | 4 | 0 |
| 500 | 0 | 0 | 2 | 0 |

Certain varieties of cucumbers set fruit without fertilization (parthenocarpic development). The English forcing cucumber used in this trial is an example of such a cucumber which produces very few seeds, however, when pollen from male flowers is transferred to female flowers by natural or artificial means fertilization and seed set results. When these normally parthenocarpic cucumbers set seed as a result of pollination, the fruit is misshapen and the general taste quality is reduced usually as a result of a bitter flavor.

Use of the compound of the invention to reduce or eliminate male flower production will remove the pollen source thereby insuring that the fruit set will be parthenocarpic and unfertilized.

EXAMPLE 42

This evaluation demonstrates the use of a compound of the invention for regulation of sex expression.

Gynoecious cucumber (Cucumis sp.) of the variety Piccadilly were treated with aqueous spray solutions of 2-chloroethylphosphonic at the first to third true leaf stage of vegetative growth. The results are recorded below.

| Treatment rate ppm | % Female flowers in first 15 nodes |
|---|---|
| Control | 63 |
| 25 | 93 |
| 50 | 100 |
| 125 | 100 |
| 250 | 100 |
| 500 | 100 |

A gynoecious cucumber plant produces only female flowers, however, a number of the new gynoecious hybrids grown under commercial field conditions have produced as high as 20 to 50% male flowers or about 50–80% female flowers. It appears that environmental conditions such as temperature and day length are, in part, responsible for expression of maleness in the normally all female gynoecious forms. Use of a compound of this invention has economic value for insuring femaleness in gynoecious cucumber varieties grown under various environmental stress conditions.

EXAMPLE 43

This evaluation demonstrates the use of a compound of the invention for accelerating fruit maturity and increasing fruit size of fruit characterized by a double-sigmoid growth development pattern.

Fig (*Ficus carnica*) trees and fruit were sprayed with aqueous solutions of 2-chloroethylphosphonic acid during the second half of growth period II. The results are recorded below.

| Treatment rate ppm | Days until ripening | Fresh weight grams | Total soluble solids % |
|---|---|---|---|
| Control | 28 | 28.7 | 7.0 |
| 250 | 7 | 84.0 | 17.4 |
| 1000 | 7 | 90.0 | 17.0 |
| 4000 | Abscissed before ripening | — | — |

Treatment with a compound of the invention during the second period of Stage II initiated the growth Period III characterized by rapid fruit enlargement of the pericarp and accelerated harvest maturity. A treatment of 4000 ppm abscised the fruit before ripening. Treated fruits developed excellent flavor as evidenced by the increase in total soluble solids.

Use of a compound of the invention offers a promising means of accelerating fig maturation and control of harvest maturity of fruit.

EXAMPLE 44

This evaluation demonstrates the use of a compound of the invention as a fruit ripening agent.

Fig (*Ficus carica*) fruit were sprayed and dipped in aqueous solutions of 2-chloroethylphosphonic acid after harvest from the tree. The results are recorded below.

| Treatment rate ppm | % Ripe fruit 7 days after treatment |
|---|---|
| Control | .6 |
| 250 | 40 |
| 1000 | 100 |
| 4000 | 100 |

Certain fruit such as figs, bananas, pears, peaches, and tomatoes must be picked in the "immature" stage before they are fully ripened in order to reduce bruising which would occur during shipment to market if the fruit were soft and ripe. Use of a compound of the invention as a ripening agent to treat "immature" fruit just prior to shipment to market or treatment after arrival at market is of economic value for inducing edible maturity without loss of quality during shipment.

EXAMPLE 45

This evaluation demonstrates the use of a compound of the invention for accelerating fruit maturity.

Figs (*Ficus carnica*) fruit were sprayed or dipped in aqueous solutions of 2-chloroethylphosphonic acid after picking. The results are recorded below.

| Treatment rate ppm | % Ripe fruit 7 days after treatment |
|---|---|
| Control | 10 |
| 500 | 80 |
| 2000 | 100 |
| 5000 | 100 |

Control of edible fruit maturity is of economic value. Often fruits must be harvested before they are ripe in order to avoid bruising and subsequent loss of fruit quality during shipment to market. However, for maximum consumer appeal fruit must be ripe when it arrives at the market or shortly thereafter, consequently, use of a compound of the invention to accelerate edible market quality of fruit is of economic importance.

EXAMPLE 46

This evaluation demonstrates the use of a compound of the invention for increasing fruit size of citrus.

Grapefruit (*Citrus paradisi*) trees were sprayed with aqueous solutions of 2-chloroethylphosphonic acid when immature fruit were ¼ to 1 inch in diameter. The results are recorded below.

| Treatment rate ppm | & Increase in fruit size at harvest |
|---|---|
| Control | 0 |
| 25 | 10 |
| 50 | 20 |
| 100 | 21 |

Use of a compound of the invention as a "sizing spray" is of economic value for increasing the yield of citrus.

EXAMPLE 47

This evaluation demonstrates the use of a compound of the invention as a growth regulator for inducing abscission of nuts.

Filbert (*Corylus* sp.) trees were sprayed prior to harvest with aqueous solutions of 2-chloroethylphosphonic acid. Post harvest treatments with 2-chloroethylphosphonic acid were applied to nuts as a solution dip. The results are recorded below.

| Treatment rate | % nut abscission following a tree shake | % increase in shuck-split, postharvest |
|---|---|---|
| Control | 25 | 23 |
| 250 ppm | 55 | 47 |
| 500 ppm | 89 | 85 |
| 1000 ppm | 94 | 96 |
| 2000 ppm | 97 | 96 |

Treatments loosened nuts on the tree and induced "shuck-split". "Shuck-split" is a term used to designate abscission of the hull (exocarp) and opening or a loosening of the nut from the outer hull. Leaf abscission was recorded with a preharvest treatment of 2000 ppm. Treated trees could be harvested one to three weeks earlier. This is of economic value since untreated nuts are often difficult to remove from the tree at optimum quality and when nuts remain on the trees for extended periods before they can be removed easily, quality of the nut is generally reduced. Postharvest dip treatments also induced abscission in the form of shuck-split enabling the nut to be removed easily from the hull.

Use of a compound of the invention as a growth regulator for inducing abscission of nuts is of economic value to harvest techniques, such as mechanical tree shaking, in order to remove the nuts at optimum harvest quality.

EXAMPLE 48

This evaluation demonstrates the use of a compound of the invention as a growth regulator increasing fruit size.

Grape (Vitis sp.) vines were sprayed three to four weeks before flowering commenced with aqueous solutions of 2-chloroethylphosphonic acid. Similar treatments were also applied at flowering time using aqueous solutions of 2-chloroethylphosphonic acid. The results are recorded below.

| Treatment rate ppm | Weight of berries in grams at harvest | | | |
|---|---|---|---|---|
| | Preflowering application | | Flowering application | |
| | Wt per berry | Cluster wt. | Wt per berry | Cluster wt. |
| Control | 1.97 | 208 | 1.91 | 232 |
| 25 | 2.64 | 316 | 2.69 | 320 |
| 50 | 2.79 | 354 | 2.77 | 381 |
| 100 | 2.63 | 325 | 2.74 | 372 |
| 500 | 2.54 | 307 | 2.63 | 350 |

Use of a compound of the invention preflowering when the clusters of rudimentary flowers appear with the leaves in early spring will reduce the number of flowers developing resulting in improved nutrition for those remaining. As a result you increase or obtain a better set of berry fruit and increase berry size and cluster weight at harvest. Application at the flowering to shatter stage reduces the crop load so that the remaining fruit will develop and mature properly. Proper cluster thinning of fruit will insure or favor the nutrition of retained clusters and berries, thereby improving berry size, coloring and maturity. Berry thinning improves quality since an over-abundance of berries makes the clusters too compact and interferes with proper coloring and delayed maturity.

Use of a compound of the invention is of economic value for increasing berry size and fruit quality.

EXAMPLE 49

This evaluation demonstrates the use of a compound of the invention for controlling vegetative growth and inducing leaf senescence.

Grape (Vitis sp.) vines were sprayed during vegetative growth periods with aqueous solutions of 2-chloroethylphosphonic acid. The results are recorded below.

| Treatment rate ppm | % Vegetative growth inhibition | | |
|---|---|---|---|
| | July spray | August spray | September spray |
| Control | 0 | 0 | 0 |
| 125 | 25 | 20 | 23 |
| 250 | 35 | 30 | 32 |
| 500 | 60 | 65 | 67 |
| 1000 | — | — | 89 |

Inhibiting vegetative growth is of economic value to reduce the amount of vine pruning required and to allow sunlight to penetrate the vines which is important for quality fruit ripening. The September spray was of particular value for accelerating senescence. Senescence is a term used to describe the processing of aging or maturing of plant tissues on an annual basis. The September spray treatments accelerated the plant senescence which was expressed by a yellowing of leaves, leaf abscission, cessation of vegetative growth and a hardening of the stem tissue. Induction of senescence is of economic value for reducing freeze damage which often occurs when grapes are allowed to continue vegetative growth into the fall or winter season.

EXAMPLE 50

This evaluation demonstrates the use of a compound of the invention as a growth regulator for inducing abscission of berries.

Grape (Vitis sp.) vines were sprayed prior to harvest with aqueous solutions of 2-chloroethylphosphonic acid. The results are recorded below.

| Treatment rate ppm | % Fruit abscission following a hand shake |
|---|---|
| Control | 3 |
| 250 | 87 |
| 500 | 89 |
| 2000 | 91 |
| 5000 | 91 |

Application of a compound of the invention as a foliar spray to leaves and fruit clusters abscissed berries from the cluster leaving the cluster stalk intact on the vine when the vines were given a light hand shake to simulate mechanical harvesting techniques. The treatment loosened the link between the berry and the stem. The fruit abscissed intact with the "brush" remaining in the fruit, the result of which was to produce a smooth, clean abscission without tearing the skin or splitting the berry. The "brush" is a term used to define an extension of the stem which extends into the berry. When untreated fruit are removed from the cluster, the brush remains attached to the stem and removal results in a tearing or splitting of the skin. Once the berry is split juice loss occurs and contamination with dirt often results. The quality of fruit abscissed with a compound of the invention will be improved by minimizing juice loss and dirt contamination since most of the abscissed berries are not split. Early senescence and leaf abscission resulted from foliar spray treatment.

Applying a compound of the invention to the fruit cluster only without contact to the foliage did not significantly affect berry abscission.

Treatment of grapes with a compound of the invention to induce grape abscission should facilitate mechanical harvesting of this crop and be of economic value for improving fruit quality.

EXAMPLE 51

This evaluation demonstrates the use of a compound of the invention for control of flowering.

Iris (*Iris tingitana*) bulbs were dipped in aqueous solutions of 2-chloroethyl phosphonic acid prior to planting. Untreated bulbs received a cold vernalization storage treatment to initiate flowering prior to planting. The results are recorded below.

| Treatment | days after treatment | | |
|---|---|---|---|
| rate ppm | 50 | 60 | 70 |
| | Number of flowers per 100 bulbs | | |
| Control | 5 | 82 | 87 |
| 250 | 10 | 89 | 95 |
| 500 | 97 | — | — |
| 1000 | 90 | 96 | — |
| 3000 | 0 | 9 | 83 |

Bulbs treated with a compound of the invention at rates of 250, 500, and 1000 ppm bloomed earlier and more uniformly than controls, which had received a cold treatment prior to planting. Treatment with 3000 ppm delayed flowering when compared to control treatments. Control of flowering is of economic value in floriculture in order to produce flowers for specific marketing intervals.

Further, the early flower initiation and development of flowering with treatments of 250, 500, and 1000 ppm in comparison to controls which had received a cold treatment indicate that the compound of the invention may substitute for the vernalizing effects of cold temperatures.

EXAMPLE 52

This evaluation again shows the use of a compound of this invention in combination with a known plant growth regulant.

Johnsongrass (*Sorghum halepense*) plants were sprayed with aqueous solutions of 2-chloroethyl-phosphonic acid just before the flower head emerged from the sheath. Observations 12 days later are recorded below.

| Treatment | Observations |
|---|---|
| Control (no treatment) | Flowering 100%, seed heads 100% developed. Plant foliage dark green, terminal shoots vigorous. Little subsurface lateral bud development. Terminals of rhizomes active near soil surface. |
| Treated with 2.24 kg/ha of 2-chloroethyl-phosphonic acid | Flowering inhibited 35%; seed heads malformed, abortion 50%; panicles failed to emerge. Terminal shoots active but leaf tips exhibiting die-back. Subsoil, numerous lateral shoots at the nodes varying in size from 0.5 to 4 cm. Unsprouted rhizome buds were normal. |
| Treated with 4.48 kg/ha of 2-chloroethyl phosphonic acid | Flowering inhibited 95%, emerged seed heads aborted and malformed; shoot tips exhibited die-back and terminal shoots dormant; numerous subsoil lateral shoots at the nodes, shoots were active and some had grown 5 to 8 cm; growth stopped when terminal bud formed. |
| Treated with 4.48 kg/ha of aminotriazole alone | Flowering inhibited 65%; seed heads developed normally; plants shorter and foliage and stems green. Numerous basal shoots; some subsoil lateral bud development. Rhizome condition was vigorous. |
| Treated with 2.24 kg/ha of 2-chloroethyl phosphonic acid plus 4.48 aminotriazole | Flowering inhibited 100%; no seed head development; plants shorter, foliage brown, bud stems green. Some basal shoots had a little green foliage. The ground rhizomes were small in diameter and subsoil. The base showed little or no rhizome development. Some of the terminals near the surface that had developed as laterals were dead. Although |

| Treatment | Observations |
|---|---|
| | other terminal rhizome buds alive, they were of low vigor. |

There was a decrease in flower and seed head development when the phosphonic derivative was applied alone. When the phosphonic derivative was applied with aminotriazole, flowering and seed head development were 100% inhibited, and the results demonstrate an interaction between the phosphonic derivative and aminotriazole resulting in improved inhibition of lateral buds and reduction of rhizome vigor.

EXAMPLE 53

This evaluation demonstrates the use of a compound of the invention as a growth regulator for inducing the rooting of cuttings as an aid to plant propagation.

Juniper (*Juniperus chinensis sargenti*) plants were sprayed with aqueous solutions of 2-chloroethylphosphonic acid 7 days prior to the removal of stem "cuttings" or "slips". A portion of these cuttings were then treated with a standard rooting hormone combination of indole-3-butyric acid and naphthylene acetic acid. Cuttings were then placed in a sand rooting media in a standard propagating bed in the greenhouse. The results are recorded below.

| Plant spray treatment rate ppm | % Cuttings with roots 10 weeks after treatment | |
|---|---|---|
| | Plant spray alone | Plant spray + NAA + IBA @ 2000 ppm |
| Control (0) | 10 | 47 |
| 100 | 14 | 44 |
| 500 | 18 | 53 |
| 1000 | 40 | 67 |
| 2000 | 54 | 73 |
| 6000 | 42 | 38 |

"Cutting or slip" is a term used to describe a portion of the plant (leaf, stem, root) which is removed from the plant for the purpose of inducing root formation and subsequently a self-supporting young plant.

Foliar spray applications with a compound of the invention prior to removal of and propagation of cuttings increased the percent of cuttings developing roots. The addition of a standard root compound to cuttings just prior to the placement in the propagation frame increase the percent rooting to a greater extent than 2-chloroethylphosphonic acid alone or the standard rooting hormones alone. With the plant spray of 2000 ppm followed by 2000 ppm of the hormone treatment a 73% rooting was obtained in contrast to 54% for the plant spray alone, and 47% for the standard hormone treatment alone.

Further, the quality of rooting was improved with plant spray treatments since roots developed all along the basal stem of the cutting on the length of the stem which was inserted into the sand media in contrast to root development primarily at the basal tip end of the cutting for the control and standard hormone treatment. Roots which develop at the basal tip end only are often broken when cuttings are removed from the media and this root damage generally results in plant loss.

EXAMPLE 54

This evaluation demonstrates the use of a compound of the invention to increase seed yields.

Ladino clover (*Trifolium repens*) plants were sprayed with aqueous solutions of 2-chloroethylphosphonic acid when 15% of the plants were flowering. The results are recorded below.

| Treatment rate | Yield lbs | % Yield increase |
|---|---|---|
| Control | 533 | — |
| 500 ppm | 661 | 24 |

When spray application was made, existing flowers were abscissed and vegetative growth (lateral branching) was stimulated. Increased and more uniform flowering on new vegetative growth following treatment produced a beneficial yield increase.

EXAMPLE 55

This evaluation demonstrates the use of a compound of the invention for removing green color or chlorophyll from citrus.

Lemon (*Citrus limon*) fruit were dipped for 10 minutes in aqueous solutions of 2-chloroethylphosphonic acid after picking. The results are recorded below.

| Treatment rate ppm | Classification % by color 7-12 days after treatment | | | |
|---|---|---|---|---|
| | Dark green | Light green | Yellow green | Fully yellow |
| Control | 90% | 10 | 0 | 0 |
| 100 | 0 | 90 | 10 | 0 |
| 500 | 0 | 0 | 90 | 10 |
| 1000 | 0 | 0 | 0 | 100 |
| 3000 | 0 | 0 | 0 | 100 |
| ethylene gas | 0 | 35 | 75 | 0 |

Citrus fruit such as lemons, oranges, grapefruit, and tangerines generally express green rind color during the early stages of maturity even though they are of edible ripe quality internally. Before marketing this fruit, it is common practice to apply ethylene gas to remove the green color or to artificially color the fruit with orange pigments. It is believed that the compounds of this invention destroy or reduce the chlorophyll in the rind allowing the expression of natural pigment color, generally orange or yellow in citrus. Although ethylene gas and compounds of the invention reduce green color in the rind through ethylene sensitive reactions within the plant tissue, the use of ethylene gas treatments require storage exposure in gas confining chambers for 24 hours or longer to induce green color removal. Treatment with a compound of the invention as an aqueous solution spray or dip does not require gas confining chambers and is easy to apply and is equally effective.

EXAMPLE 56

This evaluation demonstrates the use of a compound of the invention as a fruit ripening agent.

Mango (*Mangifera indica*) trees were sprayed with aqueous solutions of 2-chloroethylphosphonic acid just prior to normal harvest. 2-Chloroethylphosphonic acid was also applied to mango fruit postharvest by dipping the fruit in aqueous solutions. The results are recorded below.

| Treatment rate ppm | % Ripe fruit 7 days after treatment | |
|---|---|---|
| | Preharvest spray | Postharvest dip |
| Control | 0 | 10 |
| 250 | 20 | 70 |
| 500 | 60 | 100 |
| 1000 | 84 | 100 |
| 5000 | — | 100 |

The ripening of mango fruit was accelerated and increased as a result of preharvest spray applications and postharvest solution dip treatments with a compound of the invention.

EXAMPLE 57

This evaluation demonstrates the use of a compound of the invention for acceleration of flower induction.

Mango (*Mangifera indica*) trees were sprayed with aqueous solutions of 2-chloroethylphosphonic acid prior to flowering at a time corresponding to the practice of "smudging". The results are recorded below.

| Treatment rate ppm | % Acceleration of flower production |
|---|---|
| Control | 0 |
| 250 | 10 |
| 500 | 25 |
| 1000 | 32 |

Mango trees are often forced into earlier flowering by the grower practice of "smudging". "Smudging" is a term which describes the lighting of trash fires under the widespread tree branches so that these fires smoke but do not flame. "Smudging" is generally carried out without a break for fifteen consecutive days in order to induce early flower production. Use of a compound of the invention as a foliar spray application will also accelerate flower induction. Chemical treatment is simple and easy to apply and does not have the attendant fire danger which the process of smudging possesses. Early flower production is of economic value for obtaining fruit production for early markets.

EXAMPLE 58

This evaluation demonstrates the use of a compound of the invention for accelerating fruit maturity.

Melon (Cucumis sp.) plants were sprayed with aqueous solutions of 2-chloroethylphosphonic acid one to two weeks prior to normal harvest. 2-Chloroethylphosphonic acid was also applied postharvest as a solution dip to melons which had been picked. The results are recorded below.

| Treatment rate ppm | Preharvest spray | | Postharvest dip |
|---|---|---|---|
| | Yield lb/A | % Soluble solids | % Ripe fruit |
| Control | 0 | 8.1 | 50 |
| 500 | 6,000 | 15.6 | 75 |
| 1000 | 12,600 | 26.6 | 100 |
| 2000 | 13,500 | 33.6 | 100 |
| 4000 | — | — | 100 |

2-Chloroethylphosphonic acid treatments applied both preharvest and postharvest accelerated fruit maturity. Preharvest spray treatments induced early uniform maturity as evidenced by the increase in yield and percent soluble solids. Untreated plants could not be harvested until later since they were not mature. Use of a compound of the invention for accelerating fruit maturity is of economic value for increasing early fruit yields and reducing the normal number of pickings required to harvest the crop. Postharvest dip treatments increased fruit maturity. This treatment has economic value for inducing uniform ripe market quality fruit.

EXAMPLE 59

This evaluation demonstrates the use of a compound of the invention for inducing earlier fruit set and yield.

Muskmelon (*Cucumis melon*) plants were sprayed with aqueous solutions of 2-chloroethylphosphonic acid at various vegetative growth stages. The results are recorded below.

Effect of 250 ppm treatment on fruit set, sex expression and yield:

| Stage of application | No. of female flowers on stem | Successive nodes with female flowers | % Yield, stem fruit ratio | Yield Ave. fruit Wt in Kg |
|---|---|---|---|---|
| Control | 2.6 | 0 | 0 | 1.40 |
| 1 leaf | 3.5 | 9.6–12.0 | 50 | 1.65 |
| 3 leaf | 10.0 | 9.6–18.2 | 85 | 1.69 |
| 5 leaf | 10.0 | 17.2–24.8 | 86 | 1.70 |
| 1 + 3 + 5 leaf | 10.0 | 9.2–23.4 | 87 | 1.69 |

Muskmelons normally have perfect flowers (male and female in the same flower) in addition to many all male flowers. Fruit set normally occurs along lateral branches rather than on the main stem, however, treatment with a compound of the invention will induce early female flower production along the main stem which will increase early fruit set as recorded in the yield increase from the stem/fruit ratio. Yield is increased as a result of early fruit set.

Further, internode length was reduced following treatment and the dwarfing effect produced is of economic value for increasing the planting density and thereby further increasing crop yields.

EXAMPLE 60

This evaluation demonstrates the increase in pickability of fruit on trees treated with a compound of this invention.

Aqueous solutions of 2-chloroethylphosphonic acid were sprayed in run-off on to the secondary branches of olive trees bearing maturing fruit. At specified intervals thereafter, evaluations were made to determine the force required to pluck off loosened fruit. A value comparable to 250 grams weight is considered adequate to permit the use of economical mechanical shakers without incurring undesirable tree damage.

| Inspection interval after spray | Control 0 ppm | Rate 1000 ppm | 2000 ppm | 4000 ppm |
|---|---|---|---|---|
| 3 days | 521 grm* | 406 grm | 505 grm | 427 grm |
| 9 days | 467 | 451 | 332 | 162 |
| 14 days | 403 | 111 | 192 | 92 |
| 17 days | 378 | 105 | 74 | 43 |

*FRF — fruit removal force in grams

It will be seen from these results that loosening of fruit was best achieved after a week or so of treatment. At 4000 ppm., for example, mechanical harvesting was useful after 9 days. In each case, however, the treated plants required less force than the controls to pluck off the fruit. The use of compounds of this invention at rates lower than 1000 ppm. and in combination with senescence retardants are also possibilities and may be useful to remove fruit without causing leaf removal.

EXAMPLE 61

This evaluation demonstrates the use of a compound of the invention for inducing abscission.

Olive (*Olea sp.*) trees were sprayed with aqueous solutions of 2-chloroethylphosphonic acid. Results are recorded below.

| Treatment rate ppm | Fruit removal force in grams | % Increase in abscission | |
|---|---|---|---|
| | | leaves | flowers |
| Control | 537 | 0 | 0 |
| 100 | 435 | 0 | 35 |
| 500 | 285 | 50 | 50 |
| 1,000 | 105 | 75 | 100 |
| 4,000 | 43 | 100 | 100 |
| 425 + naphthaleneacetic acid @ 50 | 300 | 18 | — |

When the fruit removal force is reduced to about 250 grams or less, a high percentage of olive fruits can be removed by commercially available inertia-type tree shakers. Preharvest treatments with a compound of this invention will weaken the link between the fruit and the stem resulting in improved harvest pickability. Further, use of a compound of this invention during the flower period will thin or reduce the number of flowers thereby reducing the crop load. Reduced crop load increases tree vigor by removing the burden of maturing a heavy fruit crop. Further, fruit size is increased and annual production is improved when the tree has sufficient vigor to accumulate food reserves above what is required in energy to mature the fruit crop.

Further, the use of a compound of this invention with other chemicals such as naphthaleneacetic acid can lower leaf abscission and still reduce the fruit removal force.

EXAMPLE 62

This evaluation demonstrates the use of a compound of the invention for removal of green color or chlorophyll from fruit.

Orange (*Citrus aurantium*) fruit were treated postharvest with 2-chloroethylphosphonic acid applied as a spray, solution dip, and as a dust to the fruit. The results are recorded below.

| Treatment rate ppm | Removal of green color expressed as % Orange color 5 days after treatment | | |
|---|---|---|---|
| | Spray treatment | Dip treatment | Dust treatment |
| Control | 0 | 0 | 0 |
| 250 | 0 | 5 | 0 |
| 500 | 20 | 35 | 15 |
| 1000 | 80 | 90 | 73 |
| 2000 | 100 | 100 | 95 |

| Treatment | Removal of green color expressed as % Orange color 5 days after treatment | | |
|---|---|---|---|
| rate ppm | Spray treatment | Dip treatment | Dust treatment |
| 4000 | 100 | 100 | 100 |

Removal of green color and stimulating the expression of orange color in citrus such as oranges and tangerines is of economic value for marketable fruit appearance.

EXAMPLE 63

This evaluation demonstrates the use of a compound of the invention for stimulation of fruit abscission as an aid to mechanical harvesting.

Orange (*Citrus aurantium*), grapefruit (*Citrus paradisi*), tangerine (*Citrus reticulata*), and lemon (*Citrus limon*) trees were sprayed with aqueous solutions of 2-chloroethylphosphonic acid just prior to normal harvest. The percent fruit abscission obtained following mechanical shaking of the trees is recorded below.

| Treatment | % Fruit abscission 7 days after treatment | | | |
|---|---|---|---|---|
| rate ppm | Orange | Grapefruit | Tangerine | Lemon |
| Control | 30 | 45 | 25 | 25 |
| 100 | 45 | 60 | 45 | 43 |
| 200 | 67 | 73 | 70 | 68 |
| 500 | 85 | 89 | 83 | 86 |
| 1000 | 92 | 95 | 93 | 92 |
| 2000 | 100 | 100 | 100 | 100 |

Use of a compound of the invention loosens the link between the stem and the fruit thereby increasing the percent of fruit abscission and crop removal with mechanical harvesting equipment.

Treatments of 500, 1000 and 2000 ppm induced leaf abscission and caused some twig die-back. Treatments also accelerated color expression of natural color pigments by removing the chlorophyll or green pigment from the rind of each citrus variety.

EXAMPLE 64

This evaluation demonstrates the use of a compound of the invention for inducing fruit abscission.

Orange (Citrus sp.) trees were sprayed with aqueous solutions of 2-chloroethylphosphonic acid alone and in combination with cycloheximide just prior to harvest. The results are recorded below.

| Treatment rate | % Fruit abscission | % Rind pitting of fruit | % Leaf defoliation |
|---|---|---|---|
| Control | 0 | 0 | 0 |
| 2-chloroethylphosphonic acid @ 25 ppm | 1 | 0 | 1 |
| 2-chloroethylphosphonic acid @ 500 ppm | 50 | 0 | 70 |
| 2-chloroethylphosphonic acid @ 25 ppm + cycloheximide @ 1 ppm | 87 | less than 1 | less than 1 |
| cycloheximide @ 1 ppm | 15 | 1 | 0 |
| cycloheximide @ 5 ppm | 79 | 35 | 0 |

Treatment with 500 ppm of 2-chloroethylphosphonic acid induced fruit abscission, however, leaf defoliation accompanying treatment was severe. A rate of 25 ppm produced little or no effect with respect to abscission of leaves and fruit. No rind pitting damage was observed with either rate.

Cycloheximide applied alone at rates of 1 and 5 ppm induced fruit abscission, however, severe rind pitting damage to the fruit resulted from treatment with 5 ppm.

The combination of 2-chloroethylphosphonic acid and cycloheximide will increase fruit abscission. The link between the stem and the fruit is loosened thereby facilitating fruit removal by machine or by hand. The rates of 2-chloroethylphosphonic acid used in the combination are unique in that fruit abscission is increased over either compound alone while the undesirable side effects of rindpitting fruit damage and leaf defoliation are reduced to a non-significant level.

EXAMPLE 65

This evaluation demonstrates the use of a compound of the invention to increase crop yield and decrease lodging. An aqueous solution of 2-chloroethylphosphonic acid was sprayed on edible peas (for canning) either at the 6–9 leaflet stage, the preflowering stage or the stage at which 2 to 3 flowers had formed. Observations were made one month later and it was found that a clear anti-lodging effect was apparent in each case.

The crops were later harvested and it was found that there was an overall increase in yield from the treated plants. This was more apparent at the lower rates (say 0.85 kg/ha).

EXAMPLE 66

Another evaluation performed on peas using aqueous solutions of 2-chloroethylphosphonic acid showed an increase in the number of pods per pea plant, the actual results being as follows.

| Treatment | Rate Kg/Ha | Average number pods/plant |
|---|---|---|
| Control | — | 8.79 |
| 2-chloroethylphosphonic acid | 1.12 | 9.95 |
| 2-chloroethylphosphonic acid | 2.24 | 8.9 |
| 2-chloroethylphosphonic acid | 4.48 | 9.41 |

EXAMPLE 67

This evaluation demonstrates the use of a compound of the invention to induce freeze resistance.

Peach (Prunus sp.) trees were sprayed with aqueous solutions of 2-chloroethylphosphonic acid. The results are recorded below.

| Treatment ppm | % Fruit buds killed with $-11°$ F. |
|---|---|
| Control | 100 all dead |
| 300 | 98.1 |
| 1,000 | 91.0 |
| 2,000 | 90.1 |

Peach trees with 10% live fruit buds and subsequent fruit set will produce an economic crop compared to a complete crop loss for untreated trees.

EXAMPLE 68

This evaluation demonstrates the use of a compound of the invention for inducing freeze protection.

Peach (Prunus sp.) trees were sprayed with aqueous solutions of 2-chloroethylphosphonic acid in the spring when fruit buds had started to swell prior to blossoming. The results are recorded below.

| Treatment rate ppm | % Live fruit buds after 18° F. Freeze |
|---|---|
| Control | 2 |
| 250 | 8 |
| 500 | 15 |
| 800 | 30 |
| 1000 | 28 |
| 2000 | 27 |

One week following application of a compound of the invention a freezing situation occurred in which the temperature dropped to 18° F. Fruit buds on untreated trees were extensively killed with only 2% live buds remaining after the freeze. When only 2% of the fruit buds develop and set fruit the crop is an economic loss because of low yields produced. Treated trees with 15 to 30% live fruit buds can be expected to produce a normal economic crop for the grower.

EXAMPLE 69

This evaluation demonstrates the use of a compound of the invention for accelerating fruit maturity, development, and increasing size of fruit characterized by a double-sigmoid pattern of growth.

Peach (Prunus sp.) trees were sprayed with aqueous solutions of 2-chloroethylphosphonic acid at the midpoint of stage II which corresponds to a period of approximately 75 days after fertilization depending upon the variety. The results are recorded below.

| Treatment rate ppm | % Crop harvested | | | | Average fruit diameter (inches) |
|---|---|---|---|---|---|
| | Sept. 4 | Sept. 9 | Sept. 18 | Sept. 25 | |
| Control | 0 | 36.0 | 36.0 | 28.0 | 2.3 |
| 10 | 40.5 | 59.5 | 0 | 0 | 2.8 |
| 25 | 57.8 | 42.2 | 0 | 0 | 2.9 |
| 50 | 66.7 | 33.3 | 0 | 0 | 3.0 |
| 100 | 67.4 | 32.6 | 0 | 0 | 3.0 |

Stone fruits (drupes) such as peaches, apricots, plums, and cherries and some non-stoney fruits such as fig, grapes, and currants are characterized by a double-sigmoid fruit development curve. The double-sigmoid pattern of growth is characterized by two periods of rapid growth (Stage I and Stage III) being separated by a period of relatively slow growth (Stage II). Stage I occurs early in the fruit development cycle and is reflected by a rapid increase in pericarp and fruit enlargement shortly after fertilization. Stage III is also typified by rapid fruit enlargement just prior to normal maturity. The nature of the slow growth during Period II has not elucidated, however, it is proposed that this period which is characterized by little or no increase in fruit size or pericarp is the period in which the seed or embryo is being matured and developed. Since the period of time in which the fruit remains in Stage II has little or no value with respect to edible fruit quality, use of a compound of the invention to reduce this slow growth period and initiate rapid fruit enlargement of Stage III is of economic value for increasing fruit size and controlling harvest maturity. Further, it is postulated that use of a compound of the invention to initiate growth period III, is acting through stimulation of fruit growth via the ethylene responsive mechanism for accelerating fruit maturity.

Use of a compound of the invention as a treatment applied during the second half of Stage II initiated Stage III in peaches as shown by the accelerated crop harvest and the increase in fruit size.

EXAMPLE 70

This evaluation demonstrates the use of a compound of the invention for inducing abscission of flowers and fruit for crop thinning.

Peach (Prunus sp.) trees were sprayed with aqueous solutions of 2-chloroethylphosphonic acid at full bloom and postbloom when the ovule (seed) length of set fruit ranged from five to nine millimeters in immature fruit. The results are recorded below.

| Treatment rate ppm | Days after full bloom | % Fruit set | Fruit removed by hand | Yield lb/tree | Ave size inches |
|---|---|---|---|---|---|
| Control | 0 | 67.2 | 569 | 170 | 2.2 |
| 50 | 0 | 30.0 | 171 | 163 | 2.3 |
| 100 | 0 | 21.2 | 120 | 183 | 2.4 |
| 200 | 0 | 10.7 | 61 | 194 | 2.7 |
| 400 | 0 | 6.2 | 0 | 123 | 2.9 |
| 400 | 24[1] | 0 | 0 | 0 | 0 |
| 100 | 24[1] | 25.1 | 133 | 187 | 2.4 |
| 100 + 3 CPA[2] @ 150 | 24[1] | 20.1 | 114 | 194 | 2.6 |
| 3 CPA[2] @ 150 | 24[1] | 29.7 | 159 | 180 | 2.5 |

[1]Ovule length 7.9 mm
[2]2-(3-chlorophenoxy)propionamide

Blossom or fruit thinning of certain crops such as peaches is an accepted commercial practice required for the production of high quality fruit of marketable size. Use of a compound of the invention has economic value for crop thinning of blossoms and fruit thereby reducing the amount of hand labor required to remove unwanted fruit. Early removal of fruit with a compound of the invention enables the tree to increase fruit size which is often reflected in increased yields per tree.

Further, use of a compound of the invention in combination with another crop thinning chemical such as 2-(3-chlorophenoxy) propionamide will also produce the desired crop thinning responses.

Treatment with 400 ppm as a blossom spray overthinned the crop and caused some leaf defoliation and twig die-back, however, the vegetative effects disappeared shortly after treatment. Application of 400 ppm applied 24 days after full bloom to immature fruits with an ovule length of 7.9 mm completely eliminated fruit set and caused extensive defoliation and die-back of branches. Further, this 400 ppm treatment induced sap flow in the form of gum which extruded from the pruning cuts and lenticels of the bark.

EXAMPLE 71

This evaluation demonstrates the use of a compound of the invention as a growth regulator for control of "chilling requirements" of deciduous fruit trees.

Peaches (Prunus sp.) trees were treated with aqueous solutions of 2-chloroethylphosphonic acid after they had received 400, 600, 800 and 1000 hours of chilling cold treatment. The results are recorded below.

| Treatment | Percent shoot growth following hours of chilling | | | |
|---|---|---|---|---|
| rate ppm | 400 hrs | 600 hrs | 800 hrs | 1000 hrs |
| Control | 23 | 47 | 83 | 100 |
| 100 | 58 | 63 | 89 | 100 |
| 250 | 69 | 78 | 94 | 100 |
| 500 | 78 | 89 | 94 | 100 |
| 1000 | 84 | 91 | 92 | 93 |
| 500 + 100 ppm Gibberellic acid | 86 | 93 | 94 | 1000 |

Winter cold or chilling is needed to condition deciduous fruit trees so that their buds will open and grow normally in spring. Each winter can be characterized by the amount of chilling temperatures the plants receive and classified as either a good chilling or poor chilling winter according to the behavior of the buds of deciduous fruit trees the following spring. Peaches, depending upon variety, generally require approximately 950 hours of chilling at or below 45° F. to insure normal bud and vegetative development in the spring.

Use of a compound of the invention can lower the chilling requirement of deciduous fruit trees thereby insuring that the plant buds (fruit and vegetative) will open and grow normally in the spring.

Further, treatment with a compound of the invention may permit deciduous fruit trees to be grown in Southern areas which do not normally receive sufficient chilling for plant growth and crop production.

The application of Gibberellic acid in combination with 2-chloroethylphosphonic acid is also effective in reducing the chilling requirement of peaches.

EXAMPLE 72

This evaluation demonstrates the use of a compound of the invention for removal of apical dominance and stimulation of lateral branching.

Peanut (Arachis hypogaea) plants were sprayed during the period of vegetative growth prior to flowering with aqueous solutions of 2-chloroethylphosphonic acid. The results are recorded below.

| Treatment rate ppm | % Removal of apical dominance and stimulation of lateral branching |
|---|---|
| Control | 0 |
| 250 | 35 |
| 500 | 48 |
| 1000 | 75 |

Removal of apical dominance and stimulation of lateral branching in peanuts is of economic value for control of plant growth. Pod weight or yield is often correlated positively with the number of primary and secondary branches developed prior to flower initiation.

EXAMPLE 73

This evaluation demonstrates the use of a compound of the invention for increasing crop yields.

Peanut (Arachis hypogaea) plants were sprayed with aqueous solutions of 2-chloroethylphosphonic acid four weeks prior to harvest. The results are recorded below.

| Treatment rate ppm | Pod yields in kg/ha |
|---|---|
| Control | 1568 |
| 250 | 1620 |
| 500 | 1743 |
| 1000 | 1697 |

The yield increase was associated with an increase in the weight and number of pods and kernels per plant following a treatment with a compound of the invention.

EXAMPLE 74

This evaluation demonstrates the use of a compound of the invention for breaking seed dormancy and increasing seed germination.

Peanut (Arachis hypogaea) seeds were dipped in aqueous solutions of 2-chloroethylphosphonic acid prior to germination. The results are recorded below.

| Treatment rate ppm | % Dormant | % Germination |
|---|---|---|
| Control | 100 | 0 |
| 10 | 40 | 60 |
| 50 | 25 | 75 |
| 100 | 19 | 81 |
| 500 | 13 | 87 |

Dormant seeds such as peanuts can be induced to break dormancy and germinate when treated with a compound of the invention.

EXAMPLE 75

This evaluation demonstrates the use of a compound of the invention for inducing abscission of fruit and flowers for crop thinning.

Pear (Pyrus sp.) trees were sprayed with aqueous solutions of 2-chloroethylphosphonic acid one day prior to petal fall of flowers. The results are recorded below.

| Treatment rate ppm | % Fruit and blossom thinned | % Terminal growth inhibition | % Return bloom the following year |
|---|---|---|---|
| Control | 50 | 0 | 65 |
| 50 | 74 | 0 | 67 |
| 100 | 81 | 0 | 85 |
| 200 | 90 | 10 | 100 |
| 500 | 100 | 20 | 100 |
| 1000 | 100 | 35 | 100 |

Use of a compound of the invention to induce abscission of fruit and blossoms for crop thinning is of economic value to the grower. Fruit thinning or the early removal of a part of the developing fruit crop is an essential orchard practice if high quality fruits are to be produced and limb breakage avoided.

Further, treatment with a compound of the invention inhibited terminal shoot growth and increased the percent return bloom the year after treatment.

EXAMPLE 76

This evaluation demonstrates the use of a compound of the invention for accelerating fruit abscission as an aid to mechanical or hand harvest and acceleration of fruit maturity.

Pear (Pyrus sp.) trees were sprayed with aqueous solutions of 2-chloroethylphosphonic acid ten days prior to normal harvest. 2-Chloroethylphosphonic acid was also applied as a postharvest dip treatment after picking. The results are recorded below.

| Treatment rate ppm | Preharvest spray | | | Postharvest dip | |
|---|---|---|---|---|---|
| | % Fruit abscission following a tree shake | Fruit firmness (1b) | Color index (1) | Fruit firmness (1b) | Color index (1b) |
| Control | 2 | 19.9 | 4.8 | 19.9 | 4.8 |
| 75 | 15 | 12.1 | 3.6 | 13.2 | 3.5 |
| 250 | 35 | 6.0 | 2.3 | 6.1 | 2.3 |
| 1000 | 90 | 3.0 | 1.4 | 3.2 | 1.4 |
| 2000 | 100 | 2.9 | 1.0 | 2.0 | 1.0 |
| 4000 | 100 | 2.9 | 1.0 | 2.9 | 1.0 |

(1) Color index  5 = green   1 = yellow

Preharvest spray treatments induced fruit abscission which is of economic value to aid crop harvest. Fruit maturity was accelerated as recorded by a reduction in fruit firmness to edible quality and an increase in yellow color expression from green for untreated fruit to yellow for treated fruit. Postharvest dip treatments applied by dipping the fruit in solutions of 2-chloroethylphosphonic acid after picking also accelerated fruit maturity as observed by a reduction in fruit firmness and the expression of yellow color on treated fruit.

EXAMPLE 77

This evaluation demonstrates the use of a compound of the invention as a growth regulator for inducing abscission of nuts.

Pecans (Carya illinoensis) trees were sprayed prior to harvest with aqueous solutions of 2-chloroethylphosphonic acid. Post harvest treatments with 2-chloroethylphosphonic acid were applied to nuts as a solution dip. The results are recorded below.

| Treatment rate | % nut abscission following a tree shake | % increase in shuck-split, post harvest |
|---|---|---|
| Control | 20 | 5 |
| 250 ppm | 50 | 40 |
| 500 ppm | 90 | 82 |
| 1000 ppm | 92 | 90 |
| 2000 ppm | 96 | 97 |

Treatments loosened nuts on the tree and induced "shuck-split". "Shuck-split" is a term used to designate abscission of the hull (exocarp) and opening or a loosening of the nut from the outer hull. Leaf abscission was recorded with a preharvest treatment of 2000 ppm. Treated trees could be harvested one to three weeks earlier. This is of economic value since untreated nuts are often difficult to remove from the tree at optimum quality and when nuts remain on the tree for extended periods before they can be removed easily, quality of the nut is generally reduced. Post harvest dip treatments also induced abscission in the form of shuck-split enabling the nut to be removed easily from the hull.

Use of a compound of the invention as a growth regulator for inducing abscission of nuts is of economic value to harvest techniques, such as mechanical tree shaking, in order to remove the nuts at optimum harvest quality.

EXAMPLE 78

This evaluation demonstrates the use of a compound of the invention, in connection with well known growth retardant compounds, to increase the effect of these compounds for inhibition of grasses.

Plots of perennial grasses, mainly Agrostis spp., *Agropyron repens*, Dactylis, Lolium and *Hocus mollis*, were set up and after being cut were treated with certain compounds and combinations thereof as specified below. Two months later the plots were inspected and the following results noted.

| Treatment(s) | | Rates, kg/ha | Score EWRC Rating System |
|---|---|---|---|
| Control | — | — | 9 |
| 2-chloroethylphosphonic acid | — | 4 | 6 |
| — | maleic hydrazide | 4 | 8 |
| 2-chloroethylphosphonic acid | maleic hydrazide | 4 + 4 | 5 |
| — | FENAC | 2 | 9 |
| 2-chloroethylphosphonic acid | FENAC | 4 + 2 | 7 |
| 2-chloroethylphosphonic acid | FENAC | 8 + 2 | 5 |
| — | MSMA | 5 | 8 |
| 2-chloroethylphosphonic acid | MSMA | 4 + 5 | 5 |

FENAC = 2,3,6-trichlorophenylacetic acid (as the sodium salt)
MSMA = monosodiumacid/methane arsonate In other treatments using mixtures of 2-chloroethylphosphonic acid, FENAC and MSMA (4+2+5), scores of the order of 4 were obtained.

The scoring method used in this table is a logarithmic score based on 9 as no effect whatsoever and 1 as complete control. This system is that adopted by the European Weed Research Council.

The results demonstrate that combinations of a compound of this invention and certain known growth retardants act as stronger control agents than the growth retardant alone. It is believed that this added activity is the result of stimulation of the plant causing increased intake of the growth retardant.

EXAMPLE 79

This evaluation demonstrates the use of a compound of the invention for accelerating fruit maturity and removal of astringency from persimmon.

Persimmon (Drispyros sp.) trees were sprayed with aqueous solutions of 2-chloroethylphosphonic acid one week prior to harvest. Fruit was also removed from the tree prior to ripening and dipped in aqueous solutions of 2-chloroethylphosphonic acid. The results are recorded below.

|  | % Ripe fruit and astringency removal 7 days after treatment | | | |
|---|---|---|---|---|
|  | Preharvest | | Postharvest dip | |
| Treatment rate ppm | % Ripe | % Astringency removed | % Ripe | % Astringency removed |
| Control | 5 | 6 | 5 | 6 |
| 250 | 35 | 42 | 40 | 46 |
| 500 | 87 | 90 | 90 | 93 |
| 1000 | 100 | 100 | 100 | 100 |
| 5000 | — | — | 100 | 100 |

Persimmon fruit must be picked immature and firm in order to reduce injury during shipment to market, however, immature fruit often fails to ripen uniformly and has high astringency which sharply reduces quality. Compounds of the invention are of economic value for accelerating fruit ripening and for removing astringency of fruit when applied both pre and postharvest.

EXAMPLE 80

This evaluation demonstrates the use of a compound of the invention to induce flowering—that is to say, to "force" all the flower buds on the plants to bloom substantially simultaneously—in pineapples.

The following overall results were obtained when pineapple plants were inspected 62 days following spray treatment with the compounds specified below.

| Compound tested and pineapple variety | Application rate Lbs./Acre | % Flowering |
|---|---|---|
| Smooth Cayenne | | |
| Control | untreated | 30% |
| 2-chloroethylphosphonic acid | 1 in 50 gallons water | 100% |
|  | 2 in 50 gallons water | 100% |
|  | 4 in 50 gallons water | 100% |
| Bis(acid chloride) of 2-chloroethylphosphonic acid | 1 in 50 gallons acetone | 100% |
| Red Spanish | | |
| Control | untreated | 25% |
| 2-chloroethylphosphonic acid | 2 in 200 gallons water | 100% |
|  | 4 in 200 gallons water | 100% |
|  | 8 in 200 gallons water | 100% |

Simultaneous flowering is desirable, in that it tends to result in substantially simultaneous fruiting thus reducing the number of harvesting periods to gather the total crop.

EXAMPLE 81

This evaluation also demonstrates the use of a compound of the invention to induce flowering.

20 ml. portions of 2-chloroethylphosphonic acid in aqueous solution at the rate indicated below were applied to the crown of pineapple plants of the Smooth Cayenne Variety, and the following results were seen when the plants were inspected 89 days later.

| Application rate (ppm) | Flower induction |
|---|---|
| Control (0) | 15% |
| 1,000 | 100% |
| 10,000 | 100% |

EXAMPLE 82

This evaluation demonstrates the use of a compound of the invention as a fruit ripening agent.

Pineapple (Ananas sp.) fruit were sprayed with aqueous solutions of 2-chloroethylphosphonic acid two weeks prior to normal harvest. The results are recorded below.

| Treatment rate lb/A | Preharvest spray % Ripe fruit days after treatment | | | | | |
|---|---|---|---|---|---|---|
|  | 14 | 21 | 28 | 35 | 42 | 49 |
| Control | 0 | 10 | 40 | 30 | 9 | 7 |
| 1.0 | 30 | 40 | 30 | | | |
| 2.0 | 32 | 40 | 28 | | | |
| 4.0 | 67 | 28 | 5 | | | |
| 8.0 | 95 | 5 | | | | |

Use of a compound of the invention as a ripening agent for accelerating and concentrating harvest maturity is of economic value for reducing the number of picking times required to gather the crop.

EXAMPLE 83

This evaluation demonstrates the use of a compound of the invention as a fruit ripening agent.

Pineapples (Ananas sp.) were sprayed or dipped in aqueous solutions of 2-chloroethylphosphonic acid after harvesting the crop. The results are recorded below.

| Treatment rate ppm | % Ripe fruit 7 days after treatment |
|---|---|
| Control | 5 |
| 500 | 43 |
| 2000 | 82 |
| 4000 | 100 |

Certain fruit such as pineapples, figs, bananas, pears, peaches, and tomatoes must be picked in the "immature" stage before they are fully ripened in order to reduce bruising which would occur during shipment to market if the fruit were soft and ripe. Use of a compound of the invention as a ripening agent to treat "immature" fruit just prior to shipment to market or treatment after arrival at market is of economic value for inducing edible maturity without loss of quality during shipment.

EXAMPLE 84

This evaluation demonstrates the use of a compound of the invention for acceleration of leaf senescence and inhibition of vegetative growth.

Potato (*Solanum tuberosum*) plants were sprayed with aqueous solutions of 2-chloroethylphosphonic acid two weeks prior to harvest. The results are recorded below.

| Treatment rate lb/A | Two weeks after treatment | |
|---|---|---|
|  | % Leaf senescence | % Growth inhibition |
| Control | 0 | 0 |
| ¼ | 40 | 85 |
| ½ | 65 | 100 |
| 1 | 87 | 100 |
| 4 | 100 | 100 |

Inhibition of vegetative growth and acceleration of leaf senescence is of economic value for control of harvest. The proper time for harvesting is when the crop is mature but the actual time may be influenced by market prospects, weather conditions, and availability of labor. Potatoes are dug after the vines and leaves have senesced. This allows the skin of the tubers to "set" and reduced the degree of skinning or bruising of the tuber during harvest. Further, it is desirable to induce senescence in vines which remain alive too late in the season in order to reduce potato diseases such as late blight.

EXAMPLE 85

This evaluation demonstrates the use of a compound of the invention for increasing crop yields.

Potato (*Solanum tuberosum*) plants were sprayed with aqueous solutions of 2-chloroethylphosphonic acid when the vegetative growth of young plants was 10 to 12 centimeters in height and one week later when the vegetative growth was 12 to 15 centimeters in height. The results at harvest are recorded below.

| Treatment | Yield kg/ha following treatment | |
|---|---|---|
| rate g/ha | 10–12 cm high | 12–15 cm high |
| Control | 339.5 | 339.5 |
| 120 | 380.0 | 373.8 |
| 240 | 380.0 | 468.0 |

Use of a compound of the invention significantly increased crop yields of potatoes following treatment with 120 and 240 grams per hectare applied at both growth stages.

EXAMPLE 86

This evaluation demonstrates the use of a compound of the invention for inhibiting starch conversion in potatoes.

Potato (*Solanum tuberosum*) tubers were dipped in aqueous solutions of 2-chloroethylphosphonic acid for two minutes after harvest and prior to storage. The results are recorded below.

| Treatment rate ppm | % Inhibition of starch conversion |
|---|---|
| Control | 0 |
| 1,000 | 15 |
| 5,000 | 20 |
| 10,000 | 35 |

Newly harvested potatoes of good quality normally have a high starch content with very little sugar. When baked or boiled these potatoes have a desirable white, mealy and bland flavor quality. When processed as chips or French fries the potatoes produce a desirable light golden color.

A chemical change of starch to reducing sugars occurs when potatoes are stored at a temperature of less than 50° F. and the rate of change increases as the storage temperature is lowered. Potatoes that accumulate sugar during storage are considered somewhat undesirable for food. When baked or boiled they have not only a sweet taste but also a soggy texture and a yellowish color. When processed for chips or French fries, carmelization of the sugar by the heat of the cooking oil causes the darkening of the product. Therefore, use of a compound of the invention to inhibit starch conversion is of economic value for maintenance of potato storage quality.

EXAMPLE 87

This evaluation demonstrates the use of a compound of the invention for increasing crop yield.

Potato (*Solanum tuberosum*) plants were sprayed with aqueous solutions of 2-chloroethylphosphonic acid when the plants were in the early blossom stage. The results are recorded below.

| Treatment rate lb/A | % Yield of potato grade | | | |
|---|---|---|---|---|
| | U.S. No. 1 | Less than $1\frac{7}{8}$" diameter | Cull | Total |
| Control | 77.0 | 15.6 | 8.4 | 100 |
| $\frac{1}{8}$ | 83.0 | 25.6 | 9.4 | 118.0 |
| $\frac{1}{4}$ | 87.3 | 36.1 | 9.7 | 133.1 |
| $\frac{1}{2}$ | 77.3 | 48.3 | 9.6 | 135.2 |
| 2 | 32.5 | 36.4 | 14.3 | 83.2 |

All treatments with 2-chloroethylphosphonic acid produced a yield increase in potatoes, with the exception of the 2 lb/A rate which caused extensive inhibition of vegetative growth and reduced total potato yield.

Although an increase in U.S. No. 1 grade potatoes was obtained with chemical treatments of $\frac{1}{8}$ and $\frac{1}{4}$ lb/A the greatest increase in yield was obtained in the number of small potatoes produced. The production of small potatoes is of economic value, particularly when growing potatoes for seed. "Seed" is a term used to designate small potatoes used for planting of a potato crop. "Seed" for planting potato crops may also be obtained by cutting larger potatoes into sections, however, this is costly and the incidence of disease following planting is increased in comparison to using small intact whole potatoes.

Use of a compound of the invention is of economic value for producing "seed" potatoes.

EXAMPLE 88

This evaluation demonstrates the use of a compound of the invention for control of germination and sprout development in potatoes.

Potato (*Solanum tuberosum*) tubers were dipped in aqueous solutions of 2-chloroethylphosphonic acid for one minute just prior to planting and prior to storage for market. The results are recorded below.

| Treatment rate ppm | Number of sprouts per "seed" tuber | % Acceleration in germination |
|---|---|---|
| Control | 3 | 0 |
| 10 | 5 | 20 |
| 100 | 6 | 30 |
| 500 | 5 | 20 |
| 1,000 | 2 | 0 |
| 10,000 | 1 | 0 |

Treatment with a compound of the invention applied as a preplanting dip treatment increased the number of sprouts developing from a "seed" tuber when treated with rates of 10, 100, and 500 ppm. Further, these treatments accelerated germination of sprouting or emergence of the sprouts from the ground. An increase in the number of sprouts per plant is generally correlated to an increase in the harvested tuber yield. Early germination or sprout emergence generally results in earlier crop harvest.

Rates of 1000 ppm and 10,000 ppm reduced tuber sprouting and reduced or delayed sprout emergence. Sprout inhibition is of economic value after harvest. Inhibition of tuber sprouting is of economic value to retard sprouting in storage thereby permitting a longer interval of marketing. Sprouting in storage is undesirable since expensive labor is necessary to remove sprouts prior to marketing and there is also concern for loss of weight due to excessive shrinkage caused by translocation of materials from the tuber to the sprouts as well as a high rate of water loss through the sprouts, consequently, use of a compound of the invention can be effective at low concentrations for accelerating sprouting prior to planting and at high concentrations for inhibiting sprouting during storage.

Further, the green color characterized by certain potato varieties (i.e. Irish potatoes) following harvest is removed by dip treatments of 1000 and 10,000 ppm prior to marketing the tubers.

EXAMPLE 89

This evaluation demonstrates the use of a compound of the invention to induce ripening, color promotion and pickability.

Green peppers (Capsicum sp.) plants were sprayed just prior to harvest with aqueous solutions of 2-chloroethylphosphonic acid. Green fruit were also dipped in aqueous solutions of 2-chloroethylphosphonic acid after removal from the plant. The results are recorded below.

| Treatment | % Increase Extractable Red Color | |
|---|---|---|
| | Prior to Harvest | Post Harvest Dip |
| Control | 0 | 0 |
| 500 ppm | 60 | 65 |
| 1000 ppm | 100 | 100 |

Red Color development which is an expression of accelerated ripening was promoted by treating fruit prior to harvest and after removal from the plant by spraying or dipping in aqueous solutions of 2-chloroethylphosphonic acid. When treatments were made prior to harvest to the plant foilage with the fruit attached there was some leaf yellowing and leaf drop from the plant. Green fruit turned red in color on treated plants and were easier to pick. It was observed that treatment of pepper plants with a compound of this invention resulted in weakening the link between fruit and stalk at the normal abscission layer which made pepper fruit easier to pick.

EXAMPLE 90

This evaluation demonstrates the use of a compound of this invention used alone and in combination with another growth regulator to induce freeze resistance.

Italian prunes (Prunus sp.) were sprayed with aqueous solutions of 2-chloroethylphosphonic acid alone and in combination with gibberellic acid. The results are recorded below.

| Treatment | Rate ppm | % Fruit buds killed with −11° F. freeze five months after treatment |
|---|---|---|
| Control | — | 7.0 |
| 2-chloroethyl-phosphonic acid | 40 | 5.5 |
| 2-chloroethyl-phosphonic acid + gibberellic acid | 50 + 40 | 3.0 |

Freeze resistance of fruit buds following 2-chloroethylphosphonic acid sprays and in combination with gibberellic acid increased 13 and 23% respectively.

EXAMPLE 91

This evaluation demonstrates the use of a compound of the invention for color promotion and fruit ripening.

Pumpkin (Cucumis pepo) plants and fruit were sprayed with aqueous solutions of 2-chloroethylphosphonic acid just prior to harvest. Postharvest applications of 2-chloroethylphosphonic acid were also applied as a solution dip or spray to fruit after removal from the vine. The results are recorded below.

| Treatment rate ppm | % Orange color development of fruit 7 days after treatment | |
|---|---|---|
| | Preharvest | Postharvest |
| Control | 5 | 9 |
| 250 | 40 | 48 |
| 500 | 59 | 66 |
| 1000 | 84 | 87 |
| 2000 | 100 | 100 |

Orange color development is an indicator for maturity of pumpkin fruit. Use of a compound of the invention both pre and postharvest stimulated orange color expression. Green pumpkin fruit expressed more rapid development of uniform orange color than fruit showing some coloring at the time of treatment, however, the final orange color expression was more uniform even on fruit which had started natural color development. Although it is believed that compounds of the invention actually accelerate the coloring process by removal of green color allowing natural color expression to occur, it is also possible that compounds of the invention are stimulating or increasing pigment development directly.

EXAMPLE 92

This evaluation demonstrates the use of a compound of the invention as a growth regulator for control of harvest maturity.

Italian prune (Prunus sp.) trees were sprayed with aqueous solutions of 2-chloroethylphosphonic acid several weeks prior to harvest.

Postharvest treatments of 2-chloroethylphosphonic acid were also applied to fruit as a solution dip after removal from the tree. The results are recorded below.

| Quality data | Treatments control | 2-chloroethylphosphonic acid | | |
|---|---|---|---|---|
| | | Preharvest | | Postharvest |
| | | 40 ppm | 80 ppm | 160 ppm |
| Soluble solids % | 15.8 | 17.7 | 19.4 | 18.9 |
| Color index skin | 1.0 | 2.0 | 2.9 | 3.0 |
| % Yellow flesh | 6 | 29 | 55 | 65 |
| Firmness (lbs) | 10.9 | 9.1 | 8.0 | 7.0 |
| Size (lb/100 fruit) | 7.6 | 7.9 | 8.2 | 7.6 |
| Browning index (%) | 17.8 | 15.8 | 16.2 | 20.0 |

Color index  0 = immature green  3 = maximum purple

Preharvest applications of 2-chloroethylphosphonic acid advanced fruit maturity one to two weeks and improved fruit quality as evidenced by increases in soluble solids, skin and flesh color, and a decrease in fruit firmness. Further, preharvest treatments increased fruit size and decreased internal browning.

Postharvest solution dip treatments with a compound of the invention increased fruit quality and advanced maturity as recorded through increases in soluble solids, increased color development, and a decrease in fruit firmness.

Use of a compound of this invention for accelerating harvest maturity, increased fruit size, and improved fruit quality is of economic value for fruit production.

EXAMPLE 93

This evaluation demonstrates the use of a compound of the invention as a growth regulator for accelerating fruit maturity and increasing fruit quality when applied alone or in combination with gibberellic acid as a growth regulator.

Italian prune (Prunus sp.) trees were sprayed several weeks prior to harvest with aqueous solutions of 2-chloroethylphosphonic acid and gibberellic acid alone and in combination. The results are recorded below.

| Quality data | Control | Gibberellic acid 50 ppm | 2-chloroethyl-phosphonic acid 40 ppm | 2-chloroethylphos-phonic acid 40 ppm plus gibberellic acid 50 ppm |
|---|---|---|---|---|
| Soluble solids % | 17.2 | 17.3 | 19.4 | 19.9 |
| Color index skin | 1.6 | 1.5 | 2.5 | 2.6 |
| % Ripe in 4 days | 38 | 28 | 7.1 | 52 |
| Firmness (lb) | 8.6 | 10.9 | 7.8 | 9.0 |
| Size (lb/100 fruit) | 8.0 | 8.6 | 8.6 | 8.8 |
| Browning index % | 16.8 | 9.2 | 16.3 | 9.0 |

Gibberellic acid treatment alone is effective for reducing internal browning and increasing fruit size, however, this treatment delays harvest maturity as evidenced by no increases in soluble solids, skin color index, percent ripe fruit 4 days after treatment, and the increase in fruit firmness.

Preharvest treatment with 2-chloroethylphosphonic acid accelerated harvest maturity one to three weeks as evidenced by the increase in soluble solids, skin color index, percent of ripe fruit 4 days after treatment, and a decrease in fruit firmness. Fruit size was increased. Internal browning was only slightly decreased in comparison to gibberellic acid alone.

Internal browning of edible flesh of the fruit is a physiological problem which sharply reduced fruit quality and although gibberellic acid is effective in reducing this physiological problem, there is a strong tendency of this compound to delay harvest maturity.

When 2-chloroethylphosphonic acid was applied in combination with gibberellic acid the combination reduced internal browning, increased fruit color and soluble solids, increased fruit size and increased the percent of ripe fruit 4 days after treatment without reducing fruit firmness.

Although both 2-chloroethylphosphonic acid and gibberellic acid applied alone improve certain aspects of fruit quality the combination of both grown regulators is of economic value for producing better quality fruit.

EXAMPLE 94

This evaluation demonstrates use with other growth regulators to increase the degree of chlorosis and albanism. It is postulated the 2-chloroethylphosphonic acid increases the plant uptake of 3-amino-1,2,4-triazole.

In an evaluation using 2-chloroethylphosphonic acid in combination with 3-amino-1,2,4-triazole or ammonium thiocyanate, control of quackgrass (*Agropyron repens*) and bentgrass (*Agrostis tenuis*) was achieved at rates of from 2 kg/ha of 2-chloroethylphosphonic acid and 2 kg/ha of 3-amino-1,2,4-triazole.

EXAMPLE 95

An aqueous solution of 2-chloroethylphosphonic acid was sprayed on to growing rice (*Oryza sativa*) and the plots were later inspected for tillers. The following results were obtained.

| Rate (ppm) | Effective tillers |
|---|---|
| 0 | 100 |
| 62 | 113 |
| 125 | 118 |

Effective tillers are those developing grain heads.

The increase in tillers at the very low rates of treatment is to be noted.

EXAMPLE 96

This evaluation demonstrates the use of a compound of the invention for growth regulator control of plant height.

Roadside vegetative species such as Agropyron, Poa, Rannuculus, Cirsium, Viccia, Lolium, Dactylis, Festuca, Phleum, Cicuta, Rumex, Heracleum and Vurtica were sprayed with aqueous solutions of 2-chloroethylphosphonic acid alone and in combination with other chemicals. The results are recorded below.

| Treatment | Rate lb/A | % Height reduction of new growth |
|---|---|---|
| Control | 0 | 0 |
| 2-chloroethylphosphonic acid | 4 | 58 |
| 2-chloroethylphosphonic acid | 8 | 58 |
| 2-chloroethylphosphonic acid + MSMA [1] | 4 + 2.5 | 36 |
| 2-chloroethylphosphonic acid + MSMA | 4 + 5 | 13 |
| 2-chloroethylphosphonic acid + MSMA | 8 + 2.5 | 54 |
| 2-chloroethylphosphonic acid + MSMA | 8 + 5 | 23 |
| 2-chloroethylphosphonic acid + MH [1] | 4 + 4 | 77 |
| 2-chloroethylphosphonic acid + MH | 4 + 6 | 68 |
| 2-chloroethylphosphonic acid + MH | 8 + 4 | 83 |
| 2-chloroethylphosphonic acid + MH | 8 + 6 | 92 |

[1] Monosodium acid methanearsonate
[2] Maleic hydrazide (1,2-dihydropyridazine-3,6-dione)

The control of plant height on roadside vegetation is of economic value to reduce the number of mechanical mowings or cuttings required to maintain vegetative control.

EXAMPLE 97

This evaluation demonstrates the use of a compound of the invention for stimulating and/or increasing "sap" yield.

Rubber (Heavea sp.) plants were sprayed with aqueous solutions of 2-chloroethylphosphonic acid. 2-chloroethylphosphonic acid in a petrolatum paste was also applied to "tapped" bark area. The results are recorded below.

| Treatment | % increase in Latex yield | |
|---|---|---|
| Rate | Spray treatment | Paste treatment |
| Control | 0 | 0 |
| 1000 ppm | 75 | 0 |
| 3000 ppm | — | 5 |
| 6,000 ppm | — | 10 |
| 10,000 ppm | — | 25 |
| 20,000 ppm | — | 60 |
| 50,000 ppm | — | 100 |
| 80,000 ppm | — | 139 |
| 100,000 ppm | — | 130 |

The term "sap" is used to define "the juices of a plant" such as latex, oleoresin, oils and gums. The term "tapped" is used to define cuts made in the bark or other plant part from which sap flows.

It is common practice to "tap" rubber trees to obtain latex. Auxins such as 2,4-D and 2,4,5-T have found widespread use in rubber production for increasing latex flow. Use of a compound of this invention is also of economic value for increasing latex flow for rubber production.

EXAMPLE 98

This evaluation demonstrates the use of a compound of the invention for increasing "sap" yield.

Rubber (Ficus sp.) plants were sprayed with aqueous solutions of 2-chloroethylphosphoric acid. 2-chloroethylphosphonic acid in petrolatum paste was also applied to the area to be "tapped". The results are recorded below.

| Treatment | % increase in latex yield | |
|---|---|---|
| Rate | Spray treatment | Paste treatment |
| Control | | 0 |
| 10 | 30 | 5 |
| 100 ppm | 60 | 20 |
| 500 ppm | 95 | 50 |
| 1000 ppm | 150 | 120 |
| 10,000 ppm | 30 | 70 |

The yield of sap such as latex may be increased by use of a compound of the invention. Leaf abscission was recorded as a result of treatment with 10,000 ppm. The term "sap" is used to define "the juices of a plant" such as latex, oleoresin, oils and gums. The term "tapped" is used to define cuts made in the bark or other plant part from which sap flows.

EXAMPLE 99

This evaluation demonstrates the use of a compound of the invention to reduce stem height. Test plots of winter Rye were sprayed when the second node was visible with an aqueous acetone solution of 2-chloroethylphosphonic acid. A month later the plots were examined and the following noted.

| Treatment | Rate Kg/Ha | Stem Height Cm. |
|---|---|---|
| Control | — | 110 |
| 2-chloroethylphosphonic acid | 1 | 97 |
| 2-chloroethylphosphonic acid | 2 | 87 |
| 2-chloroethylphosphonic acid | 4 | 75 |

The reduction in stem height helps to reduce lodging tendencies.

EXAMPLE 100

This evaluation demonstrates the use of a compound of the invention for regulation of sex expression.

Squash (Cucurbita sp.) were sprayed with aqueous solutions of 2-chloroethylphosphonic acid at the one to three true leaf stage of vegetative development. The results are recorded below.

| Treatment Rate | % Female flowers in first 15 nodes |
|---|---|
| Control | 34 |
| 50 | 75 |
| 125 | 89 |
| 250 | 100 |
| 500 | 100 |

Female flower production was increased following treatments with a compound of the invention. The increase in female flower production results in an earlier and increased yield potential. The use of 2-chloroethylphosphonic acid to induce female flowers on the normally monoecious squash varieties is of economic value to hybrid seed producers since elimination of male flowers on the maternal parent will insure that all seed produced will be hybrid and eliminate the need for hand rogueing of male flowers normally practiced in seed production.

EXAMPLE 101

This evaluation demonstrates use of a compound of the invention to increase sugar beet crop yield.

2-chloroethylphosphonic acid was sprayed in aqueous solution to sugar beet twice, at an interval of three weeks. The beets were inspected six weeks after the second treatment and the results are shown below.

| Treatment | Increase in yield of Beets | Increase in recoverable sugar per acre |
|---|---|---|
| Control | — | — |
| 0.9 kg/ha (0.75 lb/acre) | +20% | +5% |

The valuable increases in yield and in recoverable sugar are apparent.

EXAMPLE 102

This evaluation demonstrates the use of a compound of the invention for "ripening" sugar cane.

Sugar cane (*Saccharum officinarum*) plants were sprayed four weeks prior to normal cane harvest with aqueous solutions of 2-chloroethylphosphonic acid. The results are recorded below.

phonic acid by spraying or dipping the leaves after harvest. The results are recorded below.

| Treatment Rate ppm | Preharvest spray | | | Postharvest spray or dip | |
|---|---|---|---|---|---|
| | No. of leaves ready for harvest per plant | Senescence[1] % | Reduction of days required for curing | Senescence[1] % | Reduction of days required for curing |
| Control | 2 | 20 | 0 | 10 | 0 |
| 500 | 4 | 40 | 2 | 20 | 1 |
| 1,000 | 6 | 63 | 3 | 37 | 2 |
| 10,000 | 10 | 78 | 5 | 66 | 4 |

[1]% Aging expressed as reduction of chlorophyll and expression of yellow color of harvest leaves.

| Treatment rate lb/A | Sucrose % fresh weight | Grams sucrose/stalk | % Terminal growth inhibition |
|---|---|---|---|
| Control | 100 | 100 | 0 |
| 2.0 | 123 | 140 | 54 |
| 4.0 | 140 | 168 | 91 |

The term "ripening" is used to denote the accumulation of sucrose in sugar cane stalks. In other trials the compounds of this invention when sprayed with aqueous solutions of 2-chloroethylphosphonic acid have increased side branching and basal shooting which may be useful to increase stalk tissue and thereby provide a larger volume of sucrose storage space.

EXAMPLE 103

This evaluation demonstrates the use of a compound of the invention for control of alternate bearing and crop thinning.

Tangerine (*Citrus reticulata*) trees were sprayed with aqueous solutions of 2-chloroethylphosphonic acid when the trees were in full bloom. The results are recorded below.

| Treatment rate ppm | % Blossom thinning | % Return bloom following year |
|---|---|---|
| Control | 0 | 10 |
| 50 | 30 | 35 |
| 100 | 45 | 35 |
| 200 | 75 | 65 |

Alternate bearing is a recognized problem in tangerines, oranges, apples, and other crops where a heavy fruit crop drains the nutrients required by the tree to produce vegetative growth for next year's fruit production. Once initiated, there is often a strong persistence of this cyclic alternate bearing pattern of heavy bearing one year and little or no production the following year.

Use of a compound of the invention to thin blossoms and thereby reduce the crop load during the heavy bearing year will enable the tree to produce vegetative growth required for production of fruit during what would be normally termed the "off bearing" year.

Use of a compound of the invention to thin the crop also increases fruit size of those fruit remaining on the tree and is of economic value for stimulating uniform annual bearing of quality size fruit.

EXAMPLE 104

This evaluation demonstrates the use of a compound of the invention for accelerating leaf senescence and curing.

Tobacco (*Nicotiana tabacum*) plants were treated with 2-chloroethylphosphonic acid two weeks prior to harvest. Tobacco leaves which had been removed from the plant were also treated with 2-chloroethylphosphonic acid by spraying or dipping the leaves after harvest. The results are recorded below.

Treatment with a compound of the invention increases the number of leaves which are ready for harvest at any one time. Normal harvesting takes place when the leaf shows numerous small patches of light yellow color and the green portion has been decreased in intensity to a light green color. As the leaves reach this stage they are removed first from the bottom of each plant (oldest leaves). Generally two or three leaves are removed at each picking which takes place at approximately weekly intervals. To harvest all of the leaves on the plant the field will normally be picked five to eight times. Use of a compound of the invention is of economic value for increasing the number of leaves per picking time and for reducing the number of field pickings required.

Further, use of a compound of the invention accelerates the curing or yellowing process thereby reducing the number of days required for the curing of harvested leaves.

The curing process expressed by a reduction of chlorophyll and an expression of yellow leaf color can also be obtained by using a compound of the invention as a postharvest spray or dip treatment.

EXAMPLE 105

This evaluation demonstrates the use of a compound of the invention for decreasing nicotine alkaloids in tobacco.

Tobacco (*Nicotiana tabacum*) plants were sprayed with aqueous solutions of 2-chloroethylphosphonic acid prior to harvest. Spray and dip treatments using 2-chloroethylphosphonic acid aqueous solutions were also applied to tobacco leaves after removal from the plant. The results are recorded below.

| Treatment rate mg/plant | Preharvest sprays % Nicotine alkaloids | | Postharvest spray or dip % Nicotine alkaloids |
|---|---|---|---|
| | Leaves | Stems | Leaves |
| Control | 2.64 | 0.63 | 2.54 |
| 90 | 1.53 | 0.33 | 1.47 |
| 120 | 1.17 | 0.21 | 1.19 |
| 150 | 0.98 | 0.16 | 0.99 |

The use of a compound of the invention for decreasing nicotine content in tobacco is of economic value for production of tobacco products with low nicotine content.

EXAMPLE 106

This evaluation demonstrates the use of the invention to increase yields and to reduce lodging.

Plots of 60 wheat plants (*Triticum aestivum*) at the four-leaf stage were treated with aqueous solutions of certain compounds of this invention, and the following results were noted when the plants were inspected four months later.

| Treatment: Compound; Rate in kg/ha | Average plot wheat head weight (grams) |
|---|---|
| Control (0) | 26.4 |
| 2-chloroethylphosphonic acid | |
| 1.12 | 41.1 |
| 2.24 | 42.5 |
| 4.48 | 44.9 |
| pyrocatechol cyclic ester of 2-chloroethylphosphonic acid | |
| 1.12 | 38.2 |
| 2.24 | 40.9 |
| 4.48 | 42.5 |

The term "lodging" describes the falling over of the plant for reasons such as weak stems, heavy head, high winds and so on. It is undesirable, since it makes harvesting very difficult.

Moderate lodging was observed in the control wheat but none was found in the treated plants.

EXAMPLE 107

This evaluation demonstrates the use of a compound of this invention to increase yields and reduce lodging.

2-Chloroethylphosphonic acid was applied to winter wheat at either the tillering stage or the early boot stage. The following was noted when the crop was harvested.

| Stage of treatment | Rate Kg/Ha | Growth inhibition % | Yield, % increase | Lodging % |
|---|---|---|---|---|
| | Control (0) | — | — | 89.1 |
| Tillering | 1 | 1.3 | 17.21 | 71.3 |
| | 2 | 2.2 | 38.15 | 58.3 |
| | 4 | 2.3 | 20.51 | 86.3 |
| | Control (0) | — | — | 95.5 |
| Early Boot | 1 | 7.3 | 36.76 | 36.6 |
| | 2 | 12.2 | 36.76 | 15.0 |
| | 4 | 15.1 | 36.90 | 5.0 |

The compound of this invention showed a shortening effect on the plants: the higher the rates and the later the date of application, the greater the shortening effect. Straw shortening observed after the first application was less than that obtained with the second treatment. The shortening effect after the second application became visible between the last leaf and the ear, i.e. there was hardly any space left between the last leaf and the ear. Also, all plots treated gave better yields than the untreated, this yield increase being better with the second treatment in the early boot stage lodging was reduced considerably, i.e. the stability of wheat was increased.

Tillers are secondary stems growing from the same seed as the main stem and at the very base of that stem. The "tillering stage" is when these tillers begin to grow.

EXAMPLE 108

This evaluation demonstrates growth regulation when using a compound of this invention. It will be noticed that the time of application is not very important though early application gives greater inhibition (manifested as a reduction in internodal distance and resulting in reduced lodging) than late application.

In this evaluation, aqueous solutions of 2-chloroethylphosphonic acid were sprayed on winter wheat on three successive occasions operated by intervals each of the order of one month. The plots were inspected three weeks after the last application and it was noted that the overall stem lengths were shorter in the treated plants than the control. Comparison of the internodes showed that the growth inhibition effect was manifested at the plant tip at the time of each application. Thus, the first application reduced the size of the lowest internode in the treated plants compared with the controls, the second application had the same effect on the middle internodes whereas the last application had the same effect on the top internodes. This is shown from the following data in which the distance from the lower edge of the ear to the first node is considered to be the first node distance; all measurements are in centimeters.

| Treatment | Rate | 1st Internodal Dist. | | 2nd Internodal Dist. | | 3rd Internodal Dist. | | 4th Internodal Dist. |
|---|---|---|---|---|---|---|---|---|
| Control | — | 49 | 11 | 28 | 10 | 18 | 5 | 13 |
| 2-chloroethylphosphonic acid | 1 | 38 | 10 | 28 | 9 | 19 | 5 | 14 |
| 2-chloroethylphosphonic acid | 2 | 34 | 8 | 28 | 8 | 20 | 6 | 14 |
| 2-chloroethylphosphonic acid | 4 | 33 | 7 | 28 | 8 | 20 | 6 | 14 |

EXAMPLE 109

This evaluation demonstrates the use of a compound of the invention to increase crop yield.

Test plots of winter wheat (variety Genesee) were planted in September and the plots were sprayed with an aqueous solution of 2-chloroethylphosphonic acid in the following May when the developing grain heads were 1 mm in length. The crop was harvested in mid-July and the following results noted.

| Treatment | Rate Kg/Ha | Yield increase % |
|---|---|---|
| Control | — | — |
| 2-chloroethylphosphonic acid | .28 | 1 |
| | .56 | 17 |
| | 1.12 | 25 |
| | 2.24 | 30 |

EXAMPLE 110

This evaluation demonstrates the use of a compound of the invention to increase crop yield and tillering, and to reduce lodging.

Spring wheat (variety Opal) was planted in test plots which were treated as follows. One set of test plots (I) was sprayed with an aqueous solution of 2-chloroethylphosphonic acid at the pre-tillering stage and a second set (II) was treated with a similar solution at the fully tillered jointing stage. The plots were inspected immediately before harvesting and rated for average lodging and average number of tillers.

The results are shown as follows

| Treatment | Plot | Dosage Kg/Ha | Yield increase % | Height | Tiller | Lodging |
|---|---|---|---|---|---|---|
| Control | I | — | — | 114 | 4.75 | 50 |
| Compound | | 1.1 | 11 | 105 | 5.28 | 50 |

-continued

The results are shown as follows:

| Treatment | Plot | Dosage Kg/Ha | Yield increase % | Height | Tiller | Lodging |
|---|---|---|---|---|---|---|
| Compound |  | 2.2 | 14 | 111 | 5.54 | 54 |
| Control | II | — | — | 106 | — | 47 |
| Compound |  | 1.1 | +17 | 99 | — | 36 |
| Compound |  | 2.2 | +33 | 89 | — | 12 |

When application was made at the pre-tillering stage (I) tillering was increased but where the plots were treated at the fully tillered stage (at which point the plants had produced the normal complement of tillers) it was not, naturally, reasonable to expect any appreciable increase in tillering.

In other tests using 2-chloroethylphosphonic acid on winter wheats of different varieties (e.g. Carsten and Genessee), summer wheat, spring wheat, and some hard wheats, increases in yields were again noted, as was a beneficial reduction effect on lodging. The same was true for other cereals particularly oats, barley, rye and rice.

EXAMPLE 111

2-chloroethylphosphonic acid was sprayed as an aqueous solution on to winter wheat infested with *Apera spica venti*. Inspection of the plots later shows suppression of the seed head formation of the Apera, in addition to the beneficial effects on the winter wheat.

EXAMPLE 112

This evaluation demonstrates the use of a compound of the invention for increased tillering and height control.

Turf grasses such as (1) Kentucky Blue grass (Poa sp.), (2) Pennlawn fescue (Festuca sp.), (3) Penncross bent (Agrostis sp.), (4) Bermuda grass (Cydonon sp.) and (5) Zoysia grass (Zoysia sp.) were sprayed with aqueous solutions of 2-chloroethylphosphonic acid. The results are recorded below.

| Treatment Rate lb/A | % increase in tillers | | | | | Average % Height reduction |
|---|---|---|---|---|---|---|
|  | (1) | (2) | (3) | (4) | (5) |  |
| 2.0 | 12 | 15 | 14 | 3 | 12 | 23 |
| 4.0 | 18 | 25 | 20 | 10 | 20 | 39 |
| 8.0 | 12 | 19 | 17 | 7 | 14 | 54 |

Increased tillers or new shoot production obtained with a compound of the invention will be of economic value for turf grass establishment by increasing the ability of the grass to spread and cover the desired surface area. Further stimulation of tillering may be obtained by mowing treated grass 3–7 days after treatment. The normal time required to produce commercial sod will be shortened as a result of rapid turf establishment. Reduction of grass height is of economic value for reducing the number of mowings required for turf maintenance.

EXAMPLE 113

This evaluation demonstrates the use of a compound of the invention as a growth regulator for inducing abscission of nuts.

Walnuts (Juglans sp.) trees were sprayed prior to harvest with aqueous solutions of 2-chloroethylphosphonic acid. Post harvest treatments with 2-chloroethylphosphonic acid were applied to nuts as a solution dip. The results are recorded below.

| Treatment Rate | % nut abscission following a tree shake | % increase in shuck-split, post harvest |
|---|---|---|
| Control | 10 | 0 |
| 250 ppm | 40 | 30 |
| 500 ppm | 85 | 75 |
| 1000 ppm | 95 | 85 |
| 2000 ppm | 95 | 97 |

Treatments loosened nuts on the tree and induced "shuck-split". "Shuck-split" is a term used to designate abscission of the hull (exocarp) and opening or a loosening of the nut from the outer hull. Leaf abscission was recorded with a preharvest treatment of 2000 ppm. Treated trees could be harvested one to three weeks earlier. This is of economic value since untreated nuts are often difficult to remove from the tree at optimum quality and when nuts remain on the tree for extended periods before they can be removed easily, quality of the nut is generally reduced. Post harvest dip treatments also induced abscission in the form of shuck-split enabling the nut to be removed easily from the hull.

Use of a compound of the invention as a growth regulator for inducing abscission of nuts is of economic value to harvest techniques, such as mechanical tree shaking, in order to remove the nuts at optimum harvest quality.

EXAMPLE 114

This evaluation demonstrates the use of a compound of the invention as a growth regulator for inducing the rooting of cuttings as an aid to plant propagation.

Yew (*Taxus cuspidata*) stem cuttings were dusted for 2 inches at the basal stem end with talc formulations containing various concentrations of 2-chloroethylphosphonic acid. The basal 2 inches of additional cuttings were quick-dipped in aqueous solutions of 2-chloroethylphosphonic acid alone and in combination with standard rooting hormones, indole-3-butyric acid and naphthylene acetic acid. Cuttings were placed in a sand media in a standard propagation bed in the greenhouse. The results are recorded below.

| Rate of 2-chloroethyl-phosphonic acid (ppm) | % Cuttings with roots 10 weeks after treatment | | 2-chloroethyl-phosphonic acid + IBA & NAA (200 ppm) Solution dip |
|---|---|---|---|
|  | 2-chloroethyl-phosphonic acid | | |
|  | Talc dust | Solution dip |  |
| Control (0) | — | 65 | 76 |
| 100 | 68 | 71 | 79 |
| 500 | 74 | 73 | 84 |
| 1000 | 79 | 80 | 87 |
| 2000 | 83 | 85 | 87 |
| 6000 | 54 | 44 | 67 |

Use of a compound of the invention generally increased the percent cuttings with roots when treatments were applied in a talc dust or aqueous solution to the basal stem portion of cuttings prior to insertion into a propagation media.

The addition of standard rooting hormones to 2-chloroethylphosphonic acid increased the rooting percentage over the use of either chemical alone.

Further, the quality of rooting was improved with 2-chloroethylphosphonic acid plant-spray treatments since roots developed all along the basal stem of the cutting on the length of the stem which was inserted into the sand media in contrast to root development primarily at the basal tip end of the cutting for the control and standard hormone treatment alone. Roots which develop at the basal dip end only are often broken when cuttings are removed from the media and this root damage generally results in plant loss.

It will be seen that the foregoing examples confirm the wide range of ethylene-type responses obtainable through the use of 2-chloroethylphosphonic acid. These examples also confirm the effectiveness of the tomato epinasty test as the standard test, usually effective within twenty-four hours of application, of an ethylene response.

The remaining examples of this application relate to compounds usable in the practice of the invention, other than 2-chloroethylphosphonic acid, although it will be noted that several of the previous examples include compounds in addition to 2-chloroethylphosphonic acid. The remaining examples also confirm the effectiveness of the tomato epinasty test in connection with compounds other than 2-chloroethylphosphonic acid. As previously stated, all compounds disclosed herein have been subjected to a twenty four hour or longer tomato epinasty test which was previously known in the art as being a reliable indicator for an ethylene reponse. The remaining examples confirm the effectiveness of the tomato epinasty test as a reliable indicator of an ethylene response.

EXAMPLE 115

This evaluation demonstrates the use of a compound of this invention to increase crop yield.

It shows that a representative cyclic ester of the invention, namely the pyrocatechol cyclic ester of 2-chloroethylphosphonic acid, can increase fruit count and weight when applied in aqueous acetone solution to *Phaseolus vulgaris* (varieties of snapbean and kidney bean) at the third trifoliate stage. It will be noted that the most effective application rate was 0.28 kg/ha.

| Plant variety | Rate | Results 7 weeks later | |
|---|---|---|---|
| | | Fruit Count | Wt. of Fruit (grams) |
| Kidney bean | Control (0) | 23 | 100 |
| | 0.28 | 32 | 136 |
| | 0.56 | 27 | 130 |
| Snapbean | Control (0) | 42 | 80 |
| | 0.28 | 110 | 190 |
| | 0.56 | 93 | 110 |

EXAMPLE 116

This evaluation demonstrates the use of other compounds of the invention to induce flowering.

20 ml. portions of the following phosphonic derivatives in aqueous solution were applied at a concentration of 10,000 ppm to pineapple plants of the Red Spanish variety and the following results were obtained.

| Compound | Flower induction |
|---|---|
| Bis(acid chloride) of 2-chloroethylphosphonic acid | 100% |
| The pyrocatechol cyclic ester of 2-chloroethyl phosphonic acid | 100% |
| The mixed butyl and 2-hydroxyphenyl diester of 2-chloroethylphosphonic acid | 100% |

The use of compounds of this invention on pineapples also has other important effects. For example, it causes general growth inhibition of the plant, giving a smaller plant and allowing more plants per acre. It also inhibits the growth of the peduncle (the stem on which the fruit grows), thus helping to prevent lodging and possible fruit damage arising therefrom (sun-scorch). Increase in the number of suckers and slips was also noted.

Inspection of a pineapple plantation used as a control plot showed that only a small percentage (about 20%) of the pineapple plants had flowered naturally in the same period.

EXAMPLE 117

This evaluation demonstrates the use of a compound of the invention to increase crop yield.

Barley plants (Hordeum spp.) were treated at the four-leaf stage with an aqueous solution of the pyrocatechol cyclic ester of 2-chloroethylphosphonic acid at a rate of 2.24 kg/ha. Four months later, the average weight of barley heads from 60 treated plants was 111.0 grams, whereas for the untreated plants the figure was 94 grams. This gives a yield increase of 18% for the treated plants over the untreated control plants.

EXAMPLE 118

This evaluation shows the use of a compound of the invention to stimulate plant growth.

Mature Johnson grass (*Sorghum halepense*) was sprayed with an aqueous solution of the pyrocatechol cyclic ester of 2-chloroethylphosphonic acid; three weeks later, the rhizomes were dug up, dried and weighed. The results are given below.

| Treatment: Rate, Kg/Ha | Rhizome dry weight, grams |
|---|---|
| Control | 1.2 |
| 1.12 | 4.5 |
| 2.24 | 4.2 |

The treatment also caused development of axillary buds at the crown area and along the rhizome axis.

EXAMPLE 119

This evaluation demonstrates the use of a compound of the invention to increase tillering and retard terminal growth.

Oat seeds (*Avena sativa*) were soaked for six hours in 50 cc of various aqueous alcohol solutions containing the pyrocatechol cyclic ester of a 2-chloroethylphosphonic acid. The seeds were planted and the plants inspected seven weeks later; the results are reported below. Economically useful biological effects—thus earlier sprouting and flowering— were observed when tubers (e.g. potato, yam and cassava) were given a soak in solutions of compounds of this invention and then planted. In the case of early potatoes especially, there seemed to be an accelaration of the plant growth which allowed the treated plants to be harvested some days earlier than the controls.

| Oats Treatment: Rate | Observations |
|---|---|
| Control (0) | Plants normal. |
| 1 ppm. of 2-chloro-ethylphosphonic acid ester | Plants 5 cm higher than controls no increase in tillering. |
| 10 ppm. | Plants same height as controls, slight increase in number of tillers. |
| 100 ppm. | Plants same height as controls, more tillers than at 10 ppm. |
| 1000 ppm. | Plants slightly shorter than controls, slightly more tillers than at 100 ppm. |

The results show an increase in the tiller count and hence potential yield, and show that at high concentrations there is a retardation in the terminal growth of the plant (thus reducing lodging tendencies).

EXAMPLE 120

This evaluation demonstrates the uses of a compound of this invention to increase lateral branching. Rooted cuttings of privot (*Ligustrum vulgare*) were sprayed with aqueous solutions of the pyrocatechol cyclic ester of 2-chloroethylphosphonic acid. Observations at six and sixteen weeks showed the following.

| Treatment | Observations Six Weeks | Sixteen Weeks |
|---|---|---|
| Control (0) | Terminal bud growth only, no lateral bud growth. | 9 shoots/plant |
| Treated with 4.48 kg/ha | Lateral bud growth at majority of nodes of stem; terminal growth retarded. | 20 shoots/plant |
| Treated with 8.96 kg/ha | Lateral bud growth observed at majority of nodes of stem in greater numbers than at 4.48 rate; terminal growth more retarded than at 4.48 rate | 20 shoots/plant |
| Treated with 17.6 kg/ha | Much lateral bud growth on stem nodes; terminal growth greatly retarded | 22 shoots/plant |

The results seen also showed that terminal growth was retarded but not completely halted. Growth continued, in fact, later in the season for the treated plants than for the controls.

EXAMPLE 121

This evaluation shows the use of a compound of the invention to increase germination rates.

Lettuce (*Lactuca sativa*) seeds were placed in petri dishes on filter paper saturated with aqueous solutions of the pyrocatechol cyclic ester of 2-chloroethylphosphonic acid. Seeds were allowed to germinate in the dark at 25° C. for 24 hours. Observations are recorded below.

| Treatment | % Germination |
|---|---|
| Control (0) | 13.1 |
| 10 ppm | 12.3 |
| 100 ppm | 13.3 |
| 1000 ppm | 31.3 |

EXAMPLE 122

This evaluation shows tobacco sucker control.

Topped tobacco (*Nicotiana tabacum*) plants (plants having had the top growth removed) were treated with an aqueous solution of 2-bromoethylphosphonic acid at the rate of 100 mgms. per plant. Ratings made two weeks later showed no sucker growth from the buds on the top part of the treated plants, whereas the control plants (topped but not treated) had suckers developing from the top three nodes but no sucker development from basal nodes. There was some development of auxiliary buds on the basal portion of the treated plants from buds close to the soil line.

EXAMPLE 123

Rose (Rosa. spp.) varieties Europeana (floribunda) and Mr. Lincoln (Hybrid-tea) were sprayed to run off with aqueous solutions of 2-iodoethyl-phosphonic acid prior to nursery field harvest. Observations made seven days later are as follows.

| Treatment | Observations | % Defoliation |
|---|---|---|
| Control (0 ppm.) | No abscission, foliage normal dark green. | 0 |
| 500 ppm. | Initial leaves at base of plant chlorotic and abscissing. | 5–10 |
| 1,500 ppm. | As for 500 ppm. | 10–25 |
| 4,500 ppm. | All leaves abscissing green. | 95–100 |
| 10,000 ppm. | All leaves abscissing green, some leaf desication. | 97–100 |

Abscission is literally the "falling off" of the leaf, as occurs naturally in autumn. The results illustrate accelerated abscission of mature foliage, which is very useful in Nurseries, for example when the plants are stored over the winter. Leaves on the plant can rot, which is undesirable.

EXAMPLE 124

This evaluation demonstrates the use of a compound of the invention to increase crop yield.

Young tomato plants (*Lycopersicon exculentum*) were sprayed at the two-leaf stage with aqueous solutions of the butyl and 2-hydroxyphenyl diester of 2-chloroethylphosphonic acid at a rate of 2.24 kg/ha. Inspection ten weeks later showed increased flowering as well as increased fruit yield.

| Treatment | No. of Flowers and Fruit |
|---|---|
| Controls | 28 |
| Treated Plants | 53 |

The treated plants were appreciably more branched, had many root primordia developed along the lower stem but were the same height as the controls.

EXAMPLE 125

This evaluation also demonstrates the use of a compound of the invention to increase potential crop yield.

Pinto bean plants (*Phaseolus vulgaris*) were sprayed at the third trifoliate stage with aqueous alcohol solutions of the 4-chloropyrocatechol cyclic ester of 2-chloroethylphosphonic acid. The results of an inspection 3 weeks later are reported below.

| Treatment Rate, Kg/Ha | Leaves | Flowers |
|---|---|---|
| Control (0) | 23 | 1 |
| 1.12 | 31 | 5 |
| 2.24 | 32 | 15 |

Axillary stimulation was also observed providing more potential sites for fruit.

EXAMPLE 126

This evaluation also demonstrates the use of a compound of the invention to increase yields and reduce lodging.

Winter wheat (Triticum spp.) plants were sprayed at early boot stage with aqueous solutions of the diphenyl ester of 2-chloroethylphosphonic acid; results are recorded below.

| Treatment: Rate kg/Ha | % Growth Inhibition | % Yield Increase | % Lodging |
|---|---|---|---|
| Control (0) | — | — | 95.5 |
| 1.12 | 7.3 | 36.7 | 36.6 |
| 2.24 | 12.2 | 36.7 | 15.0 |
| 4.48 | 15.1 | 36.9 | 5.0 |

The % growth inhibition is a measure of reduction in stem length (plant height). It is desirable so as to prevent lodging.

The term "boot stage" describes generally that stage in a cereal crop when the ear has formed within but not separated from the stem. "Early boot stage" is the beginning of that stage, "late boot stage" the end (when the ear just protrudes from the stem).

EXAMPLE 127

This evaluation shows the use of a compound of the invention to reduce stem lengths and reduce lodging. Peas (Pisum sativum) were sprayed at the 9-10 trifoliate leaf stage with aqueous solutions of the 2-chloroethyl monoester of 2-chloroethylphosphonic acid. Results were recorded one month later.

| Treatment Rate | Stem Length (% decrease) | Lodging |
|---|---|---|
| Control (0) | — | All plants lodged. |
| 0.45 | 6 | Plants slightly more erect than control |
| 2.24 | 19 | Most plants erect |
| 4.48 | 25 | All plants erect |

The results demonstrate the decrease in stem length, resulting in shorter, stronger stems and thus allowing the plants to stand erect.

EXAMPLE 128

This evaluation demonstrates the use of a compound of the invention in the "ripening" of citrus fruits.

Orange tress (Citrus sinensis): variety Valencia, and tangerine trees (Citrus reticulata), variety Robinson, were sprayed with aqueous solutions of the butyl 2-hydroxylphenyl diester of 2-chloroethylphosphonic acid. Observations are recorded below:

| Treatment | % Green | Color promotion % Degreened |
|---|---|---|
| 0 (Control) | 100 | 0 |
| 100 ppm | 0 | 100 |
| 500 ppm | 0 | 100 |
| 5000 ppm | 0 | 100 |

Oranges for example are usually "stored" on the tree, but they can turn green even though already ripe and orange. In order to make them acceptable to the public, therefore, it is necessary to de-green them or remove the chlorophyll from the rind. These results demonstrate this de-greening.

It is therefore seen that the present invention achieves a wide variety of plant growth responses in a very economical and practical way.

Without further elaboration, the foregoing will so fully illustrate our invention, that others may, by applying current or future knowledge, readily adapt the same for use under various conditions of service.

What is claimed as the invention is:

1. A method for regulating plant growth which comprises applying to the plant, including the fruits thereof, an effective but non-phytotoxic amount, with respect to the plant being treated, of a compound of the formula:

where
R is selected from the group consisting of 2-haloethyl and 2-phosphono-ethyl; and
$R_1$ and $R_2$ are selected from the group consisting of:
  (a) Chlorine atom, hydroxy group and salts thereof, except that when R is chloroethyl, $R_1$ and $R_2$ are selected from the group consisting of chlorine atom and salts of a hydroxy group;
  (b) The group —$OR_3$ and the group —O—$CH_2R_3$ where each $R_3$ is one member of the group of unsubstituted aryl, substituted aryl and heterocyclic groups;
  (c) The group —$OR_3$ and the group —O—$CH_2R_3$ where each $R_3$ is a different member of the group of hydrogen, unsubstituted alkyl, substituted alkyl, unsubstituted aryl, substituted aryl, heterocycle, alkene and alkyne with the proviso that when one $R_3$ is selected from the group of unsubstituted alkyl, substituted alkyl, alkene and alkyne, the other $R_3$ is selected from the group of unsubstituted aryl, substituted aryl and heterocycle;
  (d) Together $R_1$ and $R_2$ represent the group

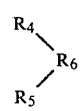

where one of $R_4$ and $R_5$ is —O— and the other is selected from the group of —O—; $OCH_2$—; —CO—O and CONH and $R_6$ represents a cyclic group selected from the group consisting of benzene, substituted benzene, heterocyclic ring and substituted heterocyclic ring;
(e) one of $R_1$ and $R_2$ is $-OR_7$ and the other is:

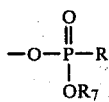

wherein each $R_7$ is the same or different and is selected from the group of hydrogen, unsubstituted alkyl, substituted alkyl, unsubstituted aryl, substituted aryl and a heterocycle group and wherein R is as defined hereinbefore.

2. The method of claim 1 wherein said method for regulating plant growth involves inducing an ethylene-type response.

3. The method of claim 1 wherein said method for regulating plant growth involves increasing yields.

4. The method of claim 1 wherein said method for regulating plant growth involves the enhancement of auxin activity.

5. The method of claim 1 wherein said method for regulating plant growth involves inhibition of terminal growth.

6. The method of claim 1 wherein said method for regulating plant growth involves control of apical dominance.

7. The method of claim 1 wherein said method for regulating plant growth involves an increase in branching.

8. The method of claim 1 wherein said method for regulating plant growth involves an increase in tillering.

9. The method of claim 1 wherein said method for regulating plant growth involves changing the biochemical composition of the plant.

10. The method of claim 1 wherein said method for regulating plant growth involves abscission of foliage, flowers and fruit.

11. The method of claim 1 wherein said method for regulating plant growth involves hastening ripening and color promotion in fruit.

12. The method of claim 1 wherein said method for regulating plant growth involves an increase in flowering and fruiting.

13. The method of claim 1 wherein said method for regulating plant growth involves abortion or inhibition of flowering and seed development.

14. The method of claim 1 wherein said method of regulating plant growth involves prevention of lodging.

15. The method of claim 1 wherein said method for regulating plant growth involves stimulation of seed germination and breaking of dormancy.

16. The method of claim 1 wherein said method for regulating plant growth involves promotion of resistance to freeze injury.

17. The method of claim 1 wherein said method for regulating plant growth involves inducing of hormone or epinasty effects.

18. The method of claim 1 wherein the compound is selected from the group consisting of:
(1) The bis(acid chloride) of 2-chloroethylphosphonic acid;
(2) The pyrocatechol cyclic ester of 2-chloroethylphosphonic acid;
(3) The 4-chloropyrocatechol cyclic ester of 2-chloroethylphosphonic acid;
(4) The mixed ethyl and 2-hydroxyphenyl diester of 2-chloroethylphosphonic acid;
(5) The mixed butyl and 2-hydroxyphenyl diester of 2-chloroethylphosphonic acid;
(6) The mixed propynyl and 2-hydroxyphenyl diester of 2-chloroethylphosphonic acid;
(7) The 2-chloroethyl monoester of 2-chloroethylphosphonic acid;
(8) 2-bromoethylphosphonic acid;
(9) The bis(phenyl)ester of 2-chloroethylphosphonic acid;
(10) The tetrachloropyrocatechol cyclic ester of 2-chloroethylphosphonic acid;
(11) 2-iodoethylphosphonic acid;
(12) The saligen cyclic ester of 2-chloroethylphosphonic acid;
(13) Salicyclic acid cyclic ester of 2-chloroethylphosphonic acid;
(14) 2-Phosphonoethylphosphonic acid;
(15) The o-hydroxyphenyl monoester of 2-chloroethylphosphonic acid;
(16) The mixed isopropyl and 2-hydroxypneyl diester of 2-chloroethylphosphonic acid;
(17) 2-fluoroethylphosphonic acid;
(18) The mixed octyl and 2-hydroxyphenyl diester of 2-chloroethylphosphonic acid;
(19) The mixed hexadecyl and 2-hydroxyphenyl diester of 2-chloroethylphosphonic acid;
(20) The mixed tridecyl and 2-hydroxyphenyl diester of 2-chloroethylphosphonic acid;
(21) The anhydride of 2-chloroethylphosphonic acid;
(22) The mixed phenyl and 2-hydroxyphenyl diester of 2-chloroethylphosphonic acid;
(23) The bis(pentachlorophenyl) ester of 2-chloroethylphosphonic acid;
(24) Salicyclic acid cyclic ester of 2-phosphonoamidic acid;
(25) The mixed phenyl and 2-hydroxyphenyl diester of 2-chloroethylphosphonic acid;
(26) 2-chloroethyl-dichloro-phosphine;
(27) The bis(pentachlorophenyl) ester of 2-chloroethylphosphonic acid;
(28) The 2,3-pyridinediol cyclic ester of 2-chloroethylphosphonic acid;
(29) The mixed butyl and 2-hydroxy phenylester of 2-chloroethylphosphonic acid;
(30) 2-chloroethylester of 2-chloroethylphosphonic acid.

19. The method of claim 1 wherein the compound is of the formula:

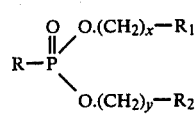

in which one of x or y is 0 and the other 0 or 1 where R is selected from the group consisting of 2-haloethyl and 2-phosphonoethyl; $R_1$ is a hydrogen atom or a substituted or unsubstituted phenyl group and $R_2$ is a hydrogen atom or a substituted or unsubstituted phenyl group or a substituted or unsubstituted, saturated or unsaturated hydrocarbon chain containing from 2 to 12 carbon atoms, except that when R is 2-chloroethyl, only one of $R_1$ and $R_2$ may be hydrogen.

20. The method of claim 1 wherein the compound is applied to the plant at a rate of from 0.1 lbs. per acre to 16 lbs. per acre.

21. The method of claim 1 wherein the compound is applied at a rate of ½ lb. per acre to 4 lbs. per acre in aqueous solution.

22. The method of claim 1 wherein the compound is 2-bromoethylphosphonic acid.

23. A method for regulating plant growth which comprises applying to the plant, including the fruits thereof, an effective but non-phytotoxic amount, with respect to the plant being treated, of 2-bromoethylphosphonic acid.

24. A method for regulating plant growth which comprises applying to the plant, including the fruits thereof, an effective but non-phytotoxic amount, with respect to the plant being treated, of a compound of the formula:

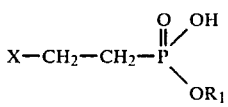

where X is halo; and $R_1$ is selected from the group consisting of:
(a) Alkyl and substituted alkyl groups having from 1 to 18 carbon atoms, and wherein the substituent is selected from the group consisting of halo and hydroxy;
(b) Phenyl and substituted phenyl wherein the substituent is selected from the group consisting of halo and hydroxy.

25. The method of claim 24 wherein X is chloro.

26. A method for regulating plant growth which comprises applying to the plant, including the fruits thereof, an effective but non-phytotoxic amount, with respect to the plant being treated, of a compound of the formula:

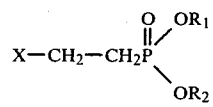

where X is halo and $R_1$ and $R_2$ are selected from the group consisting of phenyl and substituted phenyl wherein the substituent is selected from the group consisting of halo and hydroxy.

27. The method of claim 26 wherein X is chloro.

28. A method for regulating plant growth which comprises applying to the plant, including the fruits thereof, an effective but non-phytotoxic amount, with respect to the plant being treated, of a compound of the formula:

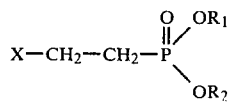

where X is halo; $R_1$ is selected from the group consisting of phenyl and substituted phenyl where the substituent is selected from the group consisting of halo and hydroxy; and $R_2$ is selected from the group consisting of alkyl and substituted alkyl and from 1 to 18 carbon atoms wherein the substituent is selected from the group consisting of halo and hydroxy.

29. The method of claim 28 wherein X is chloro.

30. A method for regulating plant growth which comprises applying to the plant, including the fruits thereof, an effective but non-phytotoxic amount, with respect to the plant being treated, of a compound of the formula:

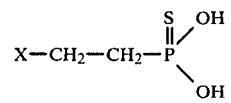

where X is halo.

31. The method of claim 30 where X is chloro.

* * * * *

UNITED STATES PATENT AND TRADEMARK OFFICE
CERTIFICATE OF CORRECTION

PATENT NO. : 4,401,454

DATED : August 30, 1983

INVENTOR(S) : Charles D. Fritz et al.

It is certified that error appears in the above—identified patent and that said Letters Patent is hereby corrected as shown below:

The heading on the first page of the patent should include the following:

"Notice: The portion of the term of this patent subsequent to April 22, 1992, has been disclaimed."

Column 3, line 10; "...sucy..." should read ...such...

Column 5, line 66; "...seet..." should read ...seed...

Column 8, line 23; "...hydrolyzed in its enzymatic systems..." should read ...hydrolyzed by its enzymatic systems...

Column 9, line 20; "...from to to 18..." should read ...from one to 18...

Column 10, line 15; "...it as been found..." should read ...it has been found...

UNITED STATES PATENT AND TRADEMARK OFFICE
CERTIFICATE OF CORRECTION

PATENT NO. : 4,401,454
DATED : August 30, 1983
INVENTOR(S) : Charles D. Fritz et al It is certified that error appears in the above—identified patent and that said Letters Patent is hereby corrected as shown below:

Column 19, line 5; "...of after picking..." should read ...or after picking...

Column 32, line 53; The word "acid" omitted after "...2-chloroethylphosphonic..."

Column 34, line 30; "& Increase in fruit size" should read: % Increase in fruit size.

Column 49, line 15; Under column heading "fruit firmness", the figure "2.0" should read: 2.9

Column 51, line 5; Column heading "Preharvest" should read: Preharvest spray.

Column 57, line 55; "...grown..." should read ...growth...

Column 64, line 63; "The results are shown as follows" should be in paragraph form, not as part of the chart.

UNITED STATES PATENT AND TRADEMARK OFFICE
CERTIFICATE OF CORRECTION

PATENT NO. : 4,401,454

DATED : August 30, 1983

INVENTOR(S) : Charles D. Fritz et al

Page 3 of 3

It is certified that error appears in the above—identified patent and that said Letters Patent is hereby corrected as shown below:

Column 65, line 1; "The results are shown as follows" should be deleted.

Column 74, line 23 (Claim 18); "...2-hydroxypneyl..." should read ...2-hydroxyphenyl...

Signed and Sealed this

Twentieth Day of December 1983

[SEAL]

Attest:

Attesting Officer

GERALD J. MOSSINGHOFF

Commissioner of Patents and Trademarks